(12) United States Patent
Dastgir et al.

(10) Patent No.: US 10,519,094 B2
(45) Date of Patent: Dec. 31, 2019

(54) METAL-CATALYZED ALKOXYCARBONYLATION OF A LACTONE

(71) Applicant: QATAR FOUNDATION FOR EDUCATION, SCIENCE AND COMMUNITY DEVELOPMENT, Doha (QA)

(72) Inventors: Sarim Dastgir, Doha (QA); Muhammed Sharif, Rostock (DE); Ralf Jackstell, Rostock (DE); Matthias Beller, Rostock (DE); Francesco Ferretti, Rostock (DE)

(73) Assignee: Qatar Foundation for Education, Science and Community Development, Doha (QA)

( * ) Notice: Subject to any disclaimer, the term of this patent is extended or adjusted under 35 U.S.C. 154(b) by 0 days.

(21) Appl. No.: 15/925,444

(22) Filed: Mar. 19, 2018

(65) Prior Publication Data

US 2018/0265449 A1    Sep. 20, 2018

Related U.S. Application Data

(60) Provisional application No. 62/473,371, filed on Mar. 18, 2017.

(51) Int. Cl.
| | |
|---|---|
| *C07C 67/36* | (2006.01) |
| *B01J 31/24* | (2006.01) |
| *C07C 29/149* | (2006.01) |
| *C07C 67/303* | (2006.01) |
| *C07C 69/602* | (2006.01) |
| *C07C 55/00* | (2006.01) |

(52) U.S. Cl.
CPC .............. *C07C 67/36* (2013.01); *B01J 31/24* (2013.01); *B01J 31/2404* (2013.01); (Continued)

(58) Field of Classification Search
CPC ....... C07C 67/36; C07C 55/00; C07C 69/602; B01J 31/24; B01J 31/2404; B01J 31/2409;
(Continued)

(56) References Cited

U.S. PATENT DOCUMENTS

| | | | |
|---|---|---|---|
| 5,817,848 A | * | 10/1998 | Kamer ................. B01J 31/2452 556/12 |
| 6,307,065 B1 | | 10/2001 | Tjaden et al. |

(Continued)

OTHER PUBLICATIONS

Behr, A., et al., Use of carbon dioxide in chemical synthesis via a lactone intermediate, 2011, Green Chemistry, The Royal Society of Chemistry, vol. 13, pp. 25-39 (Year: 2011).*

(Continued)

*Primary Examiner* — Yate' K Cutliff
(74) *Attorney, Agent, or Firm* — Richard C. Litman; Nath, Goldberg & Meyer

(57) ABSTRACT

The metal-catalyzed alkoxycarbonylation of a lactone is a method of alkoxycarbonylating a δ-lactone, specifically 3-ethylidene-6-vinyltetrahydro-2H-pyran-2-one. The method includes combining the δ-lactone with an alcohol in an organic solvent in the presence of a catalyst system that includes palladium or a salt thereof to form a reaction mixture, which is heated to 110-130° C. at a pressure of 20-50 bar for between 3-5 hours under flow of carbon monoxide gas. The product of the reaction is a substituted 2-octendioate diester. The alcohol may be methyl alcohol, n-butyl alcohol, 2-ethylhexanol, isobutyl alcohol, isopropyl alcohol, benzyl alcohol, or phenol. The solvent may be toluene, acetonitrile, or tetrahydrofuran. The method may include adding an acid to the reaction mixture, which may be dilute (about 5 mol %) sulfuric or p-toluenesulfonic acid. The catalyst system may also include a phosphine ligand.

16 Claims, 13 Drawing Sheets

1

(52) U.S. Cl.
CPC ....... *B01J 31/2409* (2013.01); *B01J 31/2414* (2013.01); *B01J 31/2438* (2013.01); *B01J 31/2452* (2013.01); *B01J 31/2457* (2013.01); *C07C 29/149* (2013.01); *C07C 67/303* (2013.01); *C07C 69/602* (2013.01); *B01J 2231/321* (2013.01); *B01J 2531/824* (2013.01); *B01J 2540/225* (2013.01); *C07C 55/00* (2013.01)

(58) Field of Classification Search
CPC ................ B01J 31/2414; B01J 31/2438; B01J 31/2452; B01J 31/2457
See application file for complete search history.

(56) References Cited

U.S. PATENT DOCUMENTS

| | | | |
|---|---|---|---|
| 6,355,802 | B1 | 3/2002 | Wuts |
| 8,445,711 | B2 | 5/2013 | Eastham et al. |
| 9,334,227 | B2 | 5/2016 | Eastham et al. |
| 2002/0019545 | A1 | 2/2002 | Kinsho et al. |
| 2014/0206893 | A1* | 7/2014 | Parton ................ C07C 67/62 560/129 |
| 2016/0031790 | A1 | 2/2016 | Molitor et al. |
| 2017/0022236 | A1* | 1/2017 | Dong .................. B01J 31/2409 |

OTHER PUBLICATIONS

Fang, X., et al, Palladium-catalyzed alkoxycarbonylation of conjugated dienes under acid-free conditions: Atom-economics synthesis of b.gamma-unsaturated esters, 2014, Carbonylation, Angewandte Communications, vol. 53, pp. 9030-9034 (Year: 2014).*

Behr, A., et al., "Use of carbon dioxide in chemical syntheses via a lactone intermediate", Green Chem. 2011, 13(1), 25-39.

Ferretti, F., et al., "Selective palladium-catalysed synthesis of diesters: alkoxycarbonylation of a CO2-butadiene derived (delta)-lactone", Green Chem, 2017, 19, 3542-3548 (with Supporting Information, S1-S12).

* cited by examiner

L20

POP =

L21

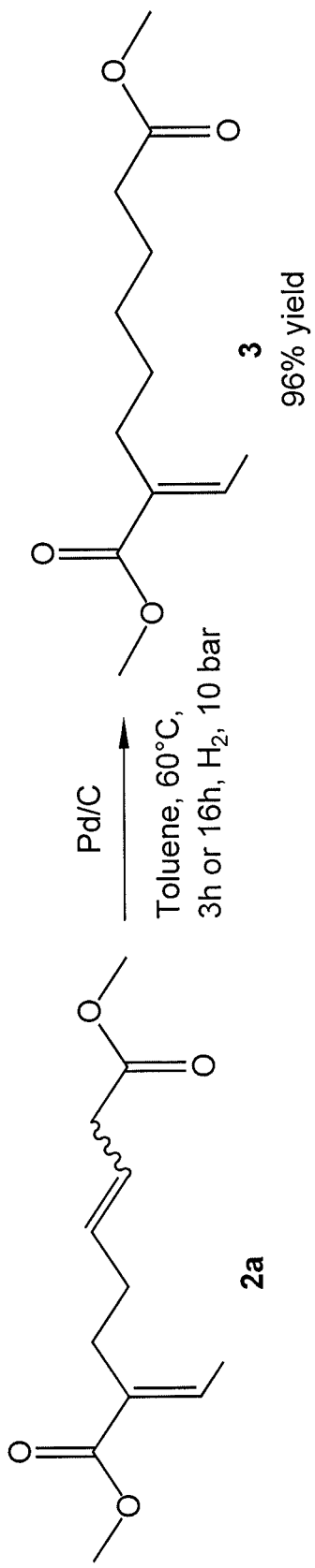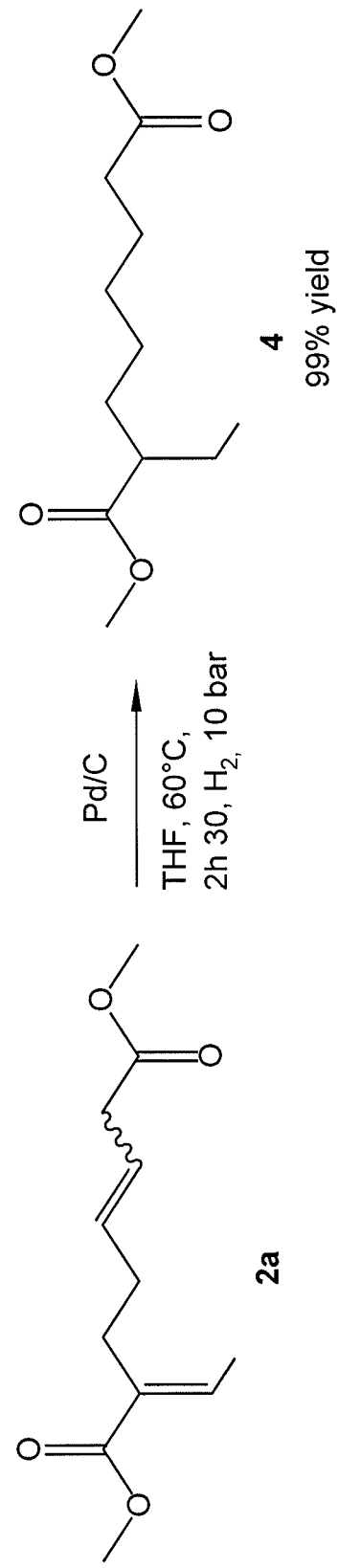
FIG. 14
FIG. 15

METAL-CATALYZED ALKOXYCARBONYLATION OF A LACTONE

CROSS-REFERENCE TO RELATED APPLICATIONS

The present patent application claims the benefit of U.S. Provisional Patent Application Ser. No. 62/473,371, filed Mar. 18, 2017.

BACKGROUND

1. Field

The disclosure of the present patent application relates to reactions of δ-lactones, and particularly to the metal-catalyzed alkoxycarbonylation of a lactone, viz., 3-ethylidene-6-vinyltetrahydro-2H-pyran-2-one.

2. Description of the Related Art

One of the most important tasks for twenty-first century scientists is dealing with challenges associated with global warming and its harmful impact on human existence on earth. Much of the global warming phenomenon is due to large quantities of carbon dioxide ($CO_2$) contaminating the planet due to dependence on energy resources from fossil fuels. As such, an important environmental challenge for the chemical industry is effective use of carbon dioxide. Despite the apparent inertness of carbon dioxide, it can be employed as a carbon source in a number of reactions. However, as opposed to stoichiometric reactions, there are few synthetic applications employing carbon dioxide in catalytic processes. There are even fewer commercialized industrial processes using such catalytic processes.

A promising way to immobilize carbon dioxide is inclusion in polymers, for instance, such polymers as $CO_2$-derived polycarbonates. Current industrial processes for the production of polycarbonates are primarily based on diols (aliphatic and/or aromatic diols) in a condensation reaction with highly toxic phosgenes. From a material properties standpoint, polycarbonates derived from such processes are much more expensive when compared with such plastics as Acrylonitrile Butadiene Styrene (ABS).

Furthermore, polymers are generally employed in all aspects of everyday life and are produced on a very large scale. Therefore, the production of polymers from carbon dioxide and a co-monomer has the potential to lead to bulk consumption of carbon dioxide. In the last decade, processes based on the reaction of carbon dioxide and epoxides for the production of polycarbonates and polyethercarbonates have been commercialized. However, polycarbonates and polyethercarbonates remain the only polymers of practical and commercial interest that include carbon dioxide.

The synthesis of other polymers or monomers derived from the direct reaction between carbon dioxide and olefins would be of particular interest, allowing the preparation of $CO_2$-based materials with different physical and mechanical properties. Although different olefins are able to react with carbon dioxide in the presence of a metal or a metal complex, in all cases, the release of the olefin-$CO_2$ adduct requires a stoichiometric reagent. Thus, direct olefin/$CO_2$ polymerization, or the synthesis of a monomer derived from olefins and carbon dioxide, which avoids the production of large amounts of waste and is produced in an economical way has proven to be a very difficult task.

The only exception to the above-described reactivity is represented by the catalytic telomerization reaction of 1,3-dienes with carbon dioxide. This reaction has been studied and optimized by different academic groups so that it is now possible to produce the δ-lactone 3-ethylidene-6-vinyltetrahydro-2H-pyran-2-one with good selectivity. The chemistry of this lactone has been extensively studied by Behr et al., "Use of carbon dioxide in chemical syntheses via a lactone intermediate", Green Chem. (2011), 13(1), 25-39, to show its commercial value, particularly studying important building block transformations from the lactone, which are shown in Table 1 below.

TABLE 1

| Reactions of 3-ethylidene-6-vinyltetrahydro-2H-pyran-2-one | | |
|---|---|---|
| Reaction | Addition of | Products |
| Hydrogenation | $H_2$ | Carboxylic acids |
| | | Saturated lactones |
| | | Diols |
| Hydroformylation | $H_2$/CO | Aldehydo-carboxylic acids |
| Hydroaminomethylation | $H_2$/CO/$HNR_2$ | Amino-lactones |
| | | Amino-carboxylic acids |
| Hydroamination | $HNR_2$ | Amino carboxylic acids |
| Alcoholysis | ROH | Hydroxy-carboxylic acids |
| | | Alkoxy-carboxylic acids |
| Hydration | $H_2O$ | Hydroxy-carboxylic acids |
| Hydrosilylation | $HSi(OEt)_3$ | Silano-carboxylic acids |
| Oxidation | $H_2O_2$ | Lactone epoxides |
| Polymerization | Dithiols, etc. | Polymers |

From Table 1, a large variety of building block molecules are accessible from the lactone via such reactions as hydrogenation, hydroformylation, hydroaminomethylation, hydroamination, alcoholysis and hydrolysis, affording carboxylic acids, saturated lactones, diols, aldehydo-lactones, amino-lactones, alkoxy-carboxylic acid esters and hydroxy-carboxylic acids.

These building blocks derived from the lactone can then be used for the manufacturing of advanced commodity polymeric materials, such as polymer processing materials, with varying properties. For instance, potential industrial targets of the highest standards include carboxylic acids, polyols, amines, aldehydes, etc. Alcohols (such as diols) and polymers are potential monomers for polyester and polyurethane chemistry, while both mono-carboxylic acids and alcohols can be used in plasticizer production.

However, Behr et al. surprisingly reported that attempts of alkoxycarbonylation of the lactone failed, leading to the alcoholized lactone instead of any carbonylation product. There remains a need for an economical alkoxycarbonylation reaction under mild conditions for the δ-lactone 3-ethylidene-6-vinyltetrahydro-2H-pyran-2-one to further encourage recycling of carbon dioxide via telomerization of 1,3 butadiene with $CO_2$. Thus, a metal catalyzed alkoxycarbonylation of lactone solving the aforementioned problems is desired.

SUMMARY

The metal-catalyzed alkoxycarbonylation of a lactone is a method of alkoxycarbonylating a δ-lactone, specifically 3-ethylidene-6-vinyltetrahydro-2H-pyran-2-one. The method includes combining the δ-lactone with an alcohol in an organic solvent in the presence of a catalyst system that includes palladium or a salt thereof to form a reaction mixture, which is heated to 110-130° C. at a pressure of 20-50 bar for between 3-5 hours under flow of carbon monoxide gas. The product of the reaction is a substituted 2-octendioate diester. The alcohol may be methyl alcohol, n-butyl alcohol, 2-ethylhexanol, isobutyl alcohol, isopropyl alcohol, benzyl alcohol, or phenol. The solvent may be toluene, acetonitrile, or tetrahydrofuran. The method may include adding an acid to the reaction mixture, which may be dilute (about 5 mol %) sulfuric or p-toluenesulfonic acid. The catalyst system may also include a phosphine ligand.

These and other features of the present disclosure will become readily apparent upon further review of the following specification and drawings.

BRIEF DESCRIPTION OF THE DRAWINGS

FIG. 14 is a first reaction scheme for further hydrogenating a diester obtained from the reaction scheme of FIG. 4.

FIG. 15 is a second reaction scheme for further hydrogenating the diester obtained from the reaction scheme of FIG. 4, resulting in formation of a saturated diester.

Similar reference characters denote corresponding features consistently throughout the attached drawings.

DETAILED DESCRIPTION OF THE PREFERRED EMBODIMENTS

The metal-catalyzed alkoxycarbonylation of a lactone is a method of alkoxycarbonylating a δ-lactone, specifically 3-ethylidene-6-vinyltetrahydro-2H-pyran-2-one. The method includes combining the δ-lactone with an alcohol in an organic solvent in the presence of a catalyst system that includes palladium or a salt thereof to form a reaction mixture, which is heated to 110-130° C. at a pressure of 20-50 bar for between 3-5 hours under flow of carbon monoxide gas. The product of the reaction is a substituted 2-octendioate diester. The alcohol may be methyl alcohol, n-butyl alcohol, 2-ethylhexanol, isobutyl alcohol, isopropyl alcohol, benzyl alcohol, or phenol. The solvent may be toluene, acetonitrile, or tetrahydrofuran. The method may include adding an acid to the reaction mixture, which may be dilute (about 5 mol %) sulfuric or p-toluenesulfonic acid. The catalyst system may also include a phosphine ligand.

The diesters produced from the method described herein may be used as monomers in polymerization reactions typical of olefins and α,β-unsaturated esters (e.g., acrylic acid derivatives), including use as co-monomers in combination with other olefins, diamines, or dialcohols to respectively give polyolefins, polyesters, and polyamides. Furthermore, the diesters of 7-ethylideneoct-3-enedioic acid or their saturated derivatives can find application as plasticizers or lubricants. In addition, the diesters of 7-ethylideneoct-3-enedioic acid or their saturated derivatives can be further used for the synthesis of 2-ethyloctane-1,8-diol, which is relevant as a monomer in polyester and polyurethane production.

Figure 1:
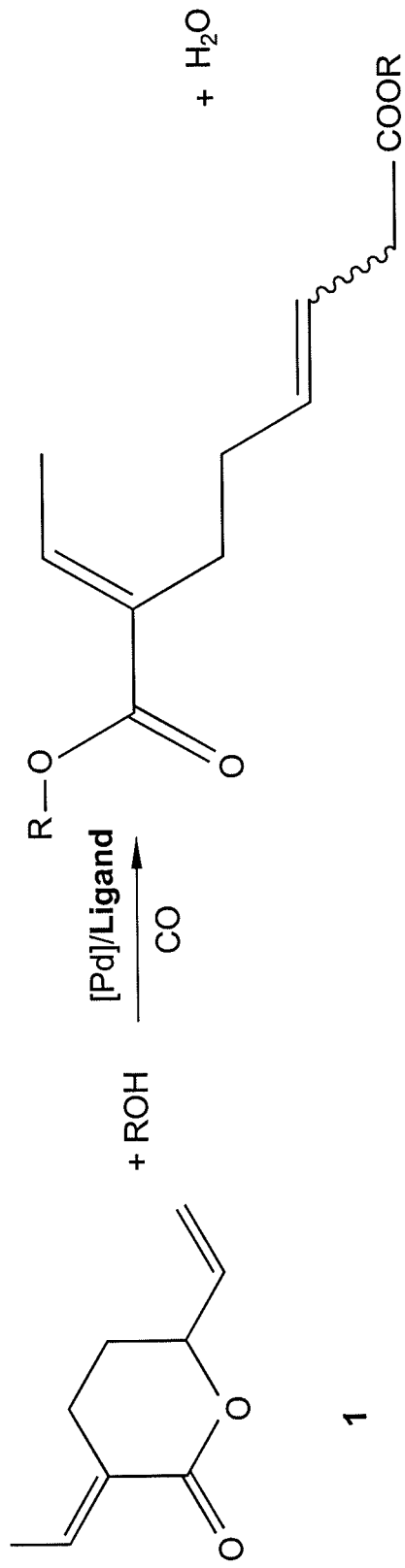
FIG. 1 is a reaction scheme for the metal-catalyzed alkoxycarbonylation of a lactone, specifically 3-ethylidene-6-vinyltetrahydro-2H-pyran-2-one.
Figure 2:
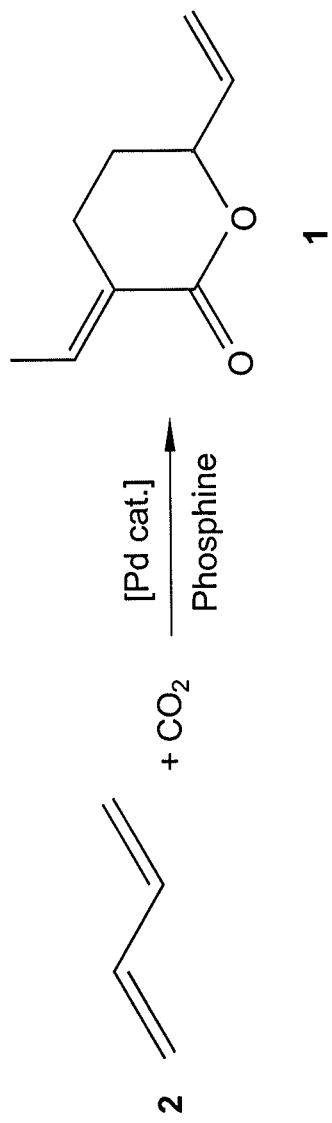
FIG. 2 is a reaction scheme for the synthesis of 3-ethylidene-6-vinyltetrahydro-2H-pyran-2-one using carbon dioxide according to the prior art.
Figure 3:
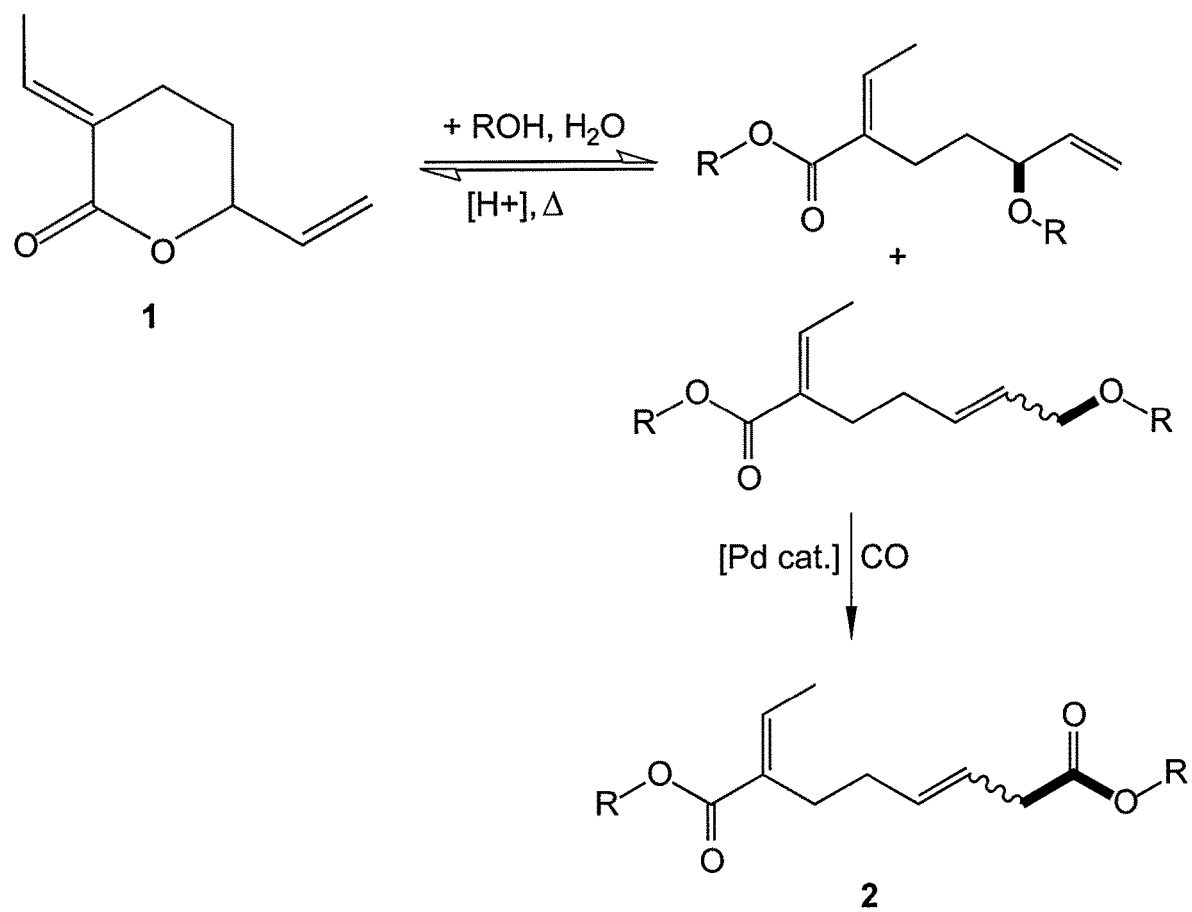
FIG. 3 is a multi-step reaction scheme for the alkoxycarbonylation of 3-ethylidene-6-vinyltetrahydro-2H-pyran-2-one to form a diester.

As noted above, the method was developed to help make the δ-lactone 1 produced by telomerization of butadiene and carbon dioxide (see the reaction scheme in FIG. 2) more commercially attractive, thereby promoting the telomerization reaction as a green chemistry method of turning carbon dioxide waste material into a renewable resource. The inventors first attempted alkoxycarboxylation of the δ-lactone 1 by heating the lactone 1 in toluene solvent with a primary alcohol and an acidic promoter. Surprisingly, it was found that this reaction produced a mixture of esters, even in the presence of palladium chloride catalyst. The reaction could be made to produce a diester product 2, but only in a multi-step reaction scheme involving alcoholysis/allylic substitution/carbonylation, as shown in FIG. 3. However, this reaction scheme is inefficient and produces unwanted byproducts.

In order to develop a more efficient method for direct alkoxycarboxylation of 3-ethylidene-6-vinyltetrahydro-2H-pyran-2-one (the δ-lactone 1), the inventors attempted using various phosphine ligands in combination with palladium chloride as the precursor catalyst. It was determined that phosphine ligand L11 produced the best selectivity and greatest yield (see the reaction scheme in FIG. 4). As the following data show, the inventors then tested the effect of various reaction conditions (temperature, pressure, acid promoter, palladium precursor, primary alcohol, etc.) to optimize reaction conditions. It was concluded that the reaction scheme shown in FIG. 4 produced the desired diester product 2 in greatest yield with best selectivity in a one-step, one-pot reaction without the production of any by-product but water, thereby providing an economical method of producing intermediates used in the commercial production of valuable polymers.

In the examples that follow, all commercial reagents were ordered from Alfa Aesar, Aldrich, TCI, or Strem. Unless otherwise stated, commercial reagents were used without purification. δ-Lactone 1 was synthesized as previously reported in Sharif et al. (Efficient and selective Palladium-catalyzed Telomerization of 1,3-Butadiene with Carbon Dioxide. ChemCatChem 2017) and kept under Ar atmosphere after distillation. Toluene, THF, acetonitrile, and methanol were collected from the solvent purification system and used under standard Schlenk technique. n-Butanol, 2-ethylhexanol, benzyl alcohol, and i-propanol were dried using standard techniques and kept under Ar atmosphere. Analytical data of literature-known compounds were in accord with reported data.

NMR spectra were recorded on Bruker AV-300, Bruker Fourier 300, or Bruker AV-400 NMR spectrometers. Multiplets were assigned as s (singlet), d (doublet), t (triplet), dd (doublet of doublet), m (multiplet), and br. s (broad singlet). All measurements were carried out at room temperature, unless otherwise stated. Mass spectra were recorded on an Agilent 6890/5973 GC-MS. High resolution mass spectra (HRMS) were recorded on Agilent 6210 Time-of-Flight LC/MS (Agilent) with electrospray ionization (ESI). The data are given as mass units per charge (m/z) and intensities of signals are given in brackets. For GC analyses, Agilent HP-7890A chromatograph equipped with a FID instrument and a HP-5 column (polydimethylsiloxane with 5% phenyl groups, 30 m, 0.32 mm i.d., 0.25 μm film thickness) was used. Unless otherwise stated, the products were isolated from the reaction mixture by column chromatography on silica gel 60, 0.063-0.2 mm, (Merck) using gradient elution from heptane to heptane/AcOEt=8:2.

Example 1

GC for Five Alcohols

Figure 4:
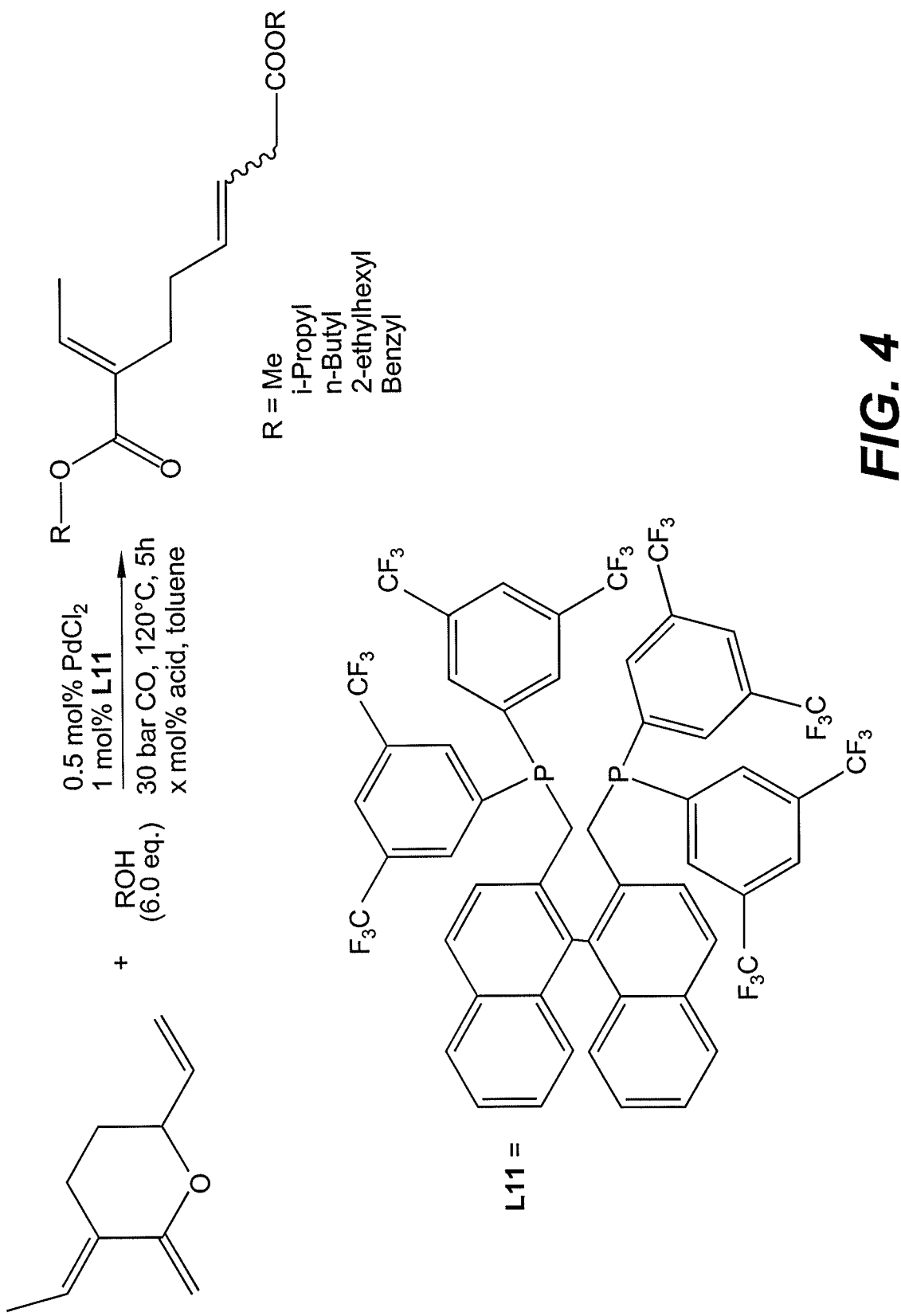
FIG. 4 is the reaction scheme for the metal-catalyzed alkoxycarbonylation of 3-ethylidene-6-vinyltetrahydro-2H-pyran-2-one using any one of five alcohols.

This example provides gas chromatography results for the separation of E/Z stereoisomer products for five alcohols (methyl alcohol, isopropyl alcohol, n-butyl alcohol, 2-ethylhexyl alcohol, and benzyl alcohol) reacted with the δ-lactone 1 under the conditions shown in the reaction scheme shown in FIG. 4. Gas chromatographic analysis was performed using the following methods.

Method 1 is an oven temperature program: 50° C.; 15° C./min to 260° C., 6 min; injection volume 1 μL with a split of 50:1. Inlet temperature 200° C.

Method 2 is an oven temperature program: 50° C.; 8° C./min to 260° C., 7 min; 8° C./min to 300° C.; injection volume 1 μL with a split of 50:1. Inlet temperature 260° C.

TABLE 2

| Key to GC Entries | |
|---|---|
| GC Entry # | Alcohol |
| 1 | Methyl |
| 2 | n-Butyl |
| 3 | 2-Ethylhexyl |
| 4 | Isopropyl |
| 5 | Benzyl |

TABLE 3

Gas Chromatography Retention Time

| GC Entry | GC Method | Compound | Retention Time (min) |
|---|---|---|---|
| 1 | 1 | 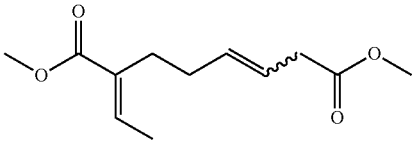<br>E/Z isomer | 11.14/11.06 |
| 2 | 1 | 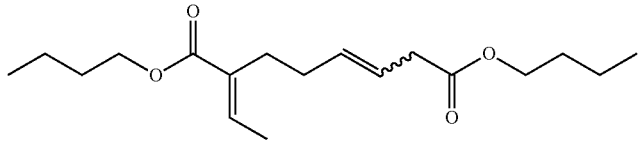<br>E/Z isomer | 14.49/14.39 |
| 3 | 2 | 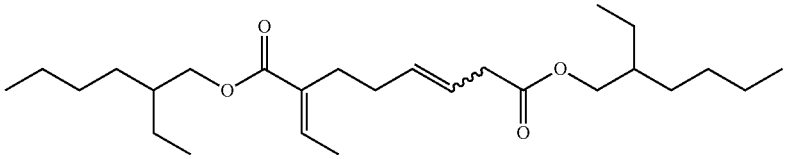<br>E/Z isomer | 31.81/31.38 |
| 4 | 1 | 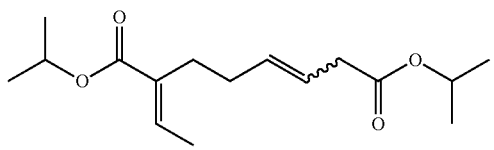<br>E/Z isomer | 12.42/12.33 |

TABLE 3-continued

Gas Chromatography Retention Time

| GC Entry | GC Method | Compound | Retention Time (min) |
|---|---|---|---|
| 5 | 2 | 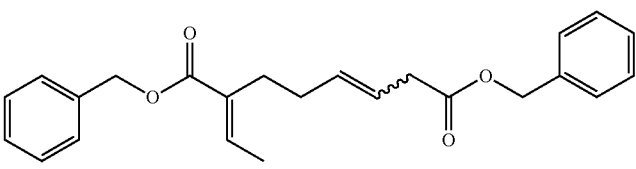<br>E/Z isomer | 35.58/35.19 |

Example 2

Spectroscopic Data for Dimethyl 7-ethylideneoct-3-enedioate

The spectroscopic data for dimethyl 7-ethylideneoct-3-enedioate (the compound shown as Entry No. 1 in Table 3) is the following.

$^1$H NMR (300 MHz, CDCl$_3$): δ 6.79 (q, J=7.1 Hz, 1H, E/Z isomers), 5.56-5.38 (m, 2H, E/Z isomers), 3.65 (s, 3H, OCH$_3$, Z isomer), 3.64 (s, 3H, OCH$_3$, E isomer), 3.60 (s, 3H, OCH$_3$, Z isomer), 3.59 (s, 3H, OCH$_3$, E/Z isomers), 3.00 (d, J=5.9 Hz, 2H, Z isomer), 2.94 (d, J=5.1 Hz, 2H, E isomer), 2.35-2.24 (m, 21-1, E/Z isomers), 2.12-1.97 (m, 2H, E/Z isomers), 1.73 (d, 3H, CHCH$_3$, Z isomer overlapped with the CHCH$_3$ signal of E isomer), 1.71 ppm (d, J=7.1 Hz, 3H, CH$_3$, E isomer).

$^{13}$C NMR (75 MHz, CDCl$_3$): δ 172.4, 172.3 (Z isomer), 168.15, 168.11 (Z isomer), 138.2 (Z isomer), 138.0, 133.8, 132.3, 132.3 (Z isomer), 132.2 (Z isomer), 122.2, 121.6 (Z isomer), 51.82 (Z isomer), 51.76, 51.6, 37.91, 32.7 (Z isomer), 31.8, 26.7 (Z isomer), 26.15, 26.09 (Z isomer), 14.4 (Z isomer), 14.3 ppm.

GC-MS-EI m/z (%): 226 (M+, 1), 194 (13), 179 (7), 162 (100), 147 (10), 134 (67), 120 (20), 107 (29), 93 (16), 91 (20), 81 (22), 71 (26), 59 (30).

ESI-HRMS calcd for C$_{12}$H$_{18}$O$_4$Na [M+Na]+: 249.10973; found: 227.10976.

Example 3

Spectroscopic Data for Diisopropyl 7-ethylideneoct-3-enedioate

The spectroscopic data for diisopropyl 7-ethylideneoct-3-enedioate (the compound shown as Entry No. 4 in Table 3) is the following.

$^1$H NMR (300 MHz, CDCl$_3$): δ 6.81 (q, J=7.1 Hz, 1H, E/Z isomers), 5.67-5.33 (m, 2H, E/Z isomers), 5.07-4.86 (m, 2H, E/Z isomers), 3.01 (d, J=5.7 Hz, 2H, Z isomer), 2.94 (d, J=5.2 Hz, 2H, E isomer), 2.38-2.28 (m, 2H, E/Z isomers), 2.20-2.02 (m, 2H, E/Z isomers), 1.76 (d, 3H, CHCH$_3$, Z isomer overlapped with the CHCH$_3$ signal of E isomer), 1.74 (d, J=7.1 Hz, 3H, CHCH$_3$, E isomer), 1.30-0.81 ppm (m, 12H, E/Z isomers).

$^{13}$C NMR (75 MHz, CDCl$_3$): δ 171.5, 167.2, 137.4 (Z isomer), 137.2, 133.6, 132.9, 132.0 (Z isomer), 122.4, 121.9 (Z isomer), 67.8, 67.8, 67.5, 67.4, 38.4, 33.2 (Z isomer), 31.8, 26.8 (Z isomer), 26.2, 26.1 (Z isomer), 21.9, 21.8, 14.3 (Z isomer), 14.3 ppm.

GCMS-EI m/z (%): 285 (M+, 0.3), 240 (2), 222 (5), 198 (4), 194 (4), 180 (25), 162 (67), 153 (11), 134 (46), 107 (27), 93 (16), 81 (16), 67 (7), 54 (35), 43 (100).

ESI-HRMS calcd for C$_{16}$H$_{26}$O$_4$Na [M+Na]+: 305.17233; found: 305.17229.

Example 4

Spectroscopic Data for Bis(2-ethylhexyl) 7-ethylideneoct-3-enedioate

The spectroscopic data for bis(2-ethylhexyl) 7-ethylideneoct-3-enedioate (the compound shown as Entry No. 3 in Table 3) is the following.

$^1$H NMR (300 MHz, CDCl$_3$): δ 6.84 (q, J=7.1 Hz, 1H, E/Z isomers), 5.63-5.33 (m, 2H, E/Z isomers), 4.08-3.89 (m, 4H, E/Z isomers), 3.05 (d, J=5.3 Hz, 2H, Z isomer), 2.99 (d, J=5.3 Hz, 2H, Z isomer), 2.50-2.23 (m, 2H, E/Z isomers), 2.19-2.01 (m, 2H, E/Z isomers), 1.79 (d, 3H, CHCH$_3$, Z isomer overlapped with the CHCH$_3$ signal of E isomer), 1.76 (d, J=7.2 Hz, 3H, CHCH$_3$, E isomer), 1.65-1.44 (m, 2H, E/Z isomers), 1.43-1.12 (m, 16H, E/Z isomers), 0.98-0.77 ppm (m, 12H, E/Z isomers).

$^{13}$C NMR (75 MHz, CDCl$_3$): δ 172.2, 167.8, 137.8 (Z isomer), 137.6, 133.6, 132.6, 132.1 (Z isomer), 122.4, 121.7 (Z isomer), 67.0, 66.6, 38.9, 38.7, 38.2, 33.0 (Z isomer), 31.9, 30.6, 30.4, 28.98, 28.91, 26.8 (Z isomer), 26.3, 26.1 (Z isomer), 24.0, 23.8, 23.0, 14.4 (Z isomer), 14.3, 14.0, 11.1, 11.0 ppm.

GCMS-EI m/z (%): 422 (M+, 0.3), 292 (4), 264 (4), 198 (4), 180 (44), 162 (100), 152 (12), 134 (29), 107 (15), 81 (8), 71 (44), 57 (69), 43 (41).

EI-HRMS calcd. for C$_{26}$H$_{46}$O$_4$ [M]+: 422.33906; found: 422.33917.

Example 5

Spectroscopic Data for Dibenzyl 7-ethylideneoct-3-enedioate

The spectroscopic data for dibenzyl 7-ethylideneoct-3-enedioate (the compound shown as Entry No. 5 in Table 3) is the following.

$^1$H NMR (300 MHz, CDCl$_3$): δ 7.39-7.21 (m, 10H, E/Z isomers), 6.92 (q, J=7.1 Hz, 1H, E/Z isomers), 5.67-5.43 (m, 2H, E/Z isomers), 5.16 (s, 2H, E/Z isomers), 5.10 (s, 2H, E/Z isomers), 3.07 (d, J=5.2 Hz, 2H, Z isomer), 3.03 (d, J=4.2 Hz, 2H, E isomer), 2.50-2.30 (m, 2H E/Z isomers), 2.21-2.08 (m, 2H E/Z isomers), 1.75 (d, J=7.1 Hz, 3H, CHCH$_3$, Z isomer overlapped with the CHCH$_3$ signal of E isomer), 1.74 ppm (d, J=7.2 Hz, 3H, CHCH$_3$, Z isomer overlapped with the CHCH$_3$ signal of E isomer).

$^{13}$C NMR (75 MHz, CDCl$_3$): δ 171.7, 171.6 (Z isomer), 167.3, 138.5 (Z isomer), 138.4, 136.4, 135.9, 133.8, 132.3, 132.2 (Z isomer), 128.5, 128.2, 128.0, 127.9, 122.2, 121.6 (Z isomer), 66.3, 66.1, 38.0, 32.8 (Z isomer), 31.8, 26.8 (Z isomer), 26.1, 26.0 (Z isomer), 14.3 ppm.

GCMS-EI m/z (%): 287 (2), 269 (3), 251 (3), 223 (2), 181 (2), 163 (4), 107 (2), 91 (100), 65 (7).

ESI-HRMS calcd for C$_{24}$H$_{26}$O$_4$Na [M+Na]+: 401.17233; found: 401.17243.

Example 6

Spectroscopic Data for Dibutyl 7-ethylideneoct-3-enedioate

The spectroscopic data for dibutyl 7-ethylideneoct-3-enedioate (the compound shown as Entry No. 2 in Table 3) is the following.

$^1$H NMR (300 MHz, CDCl$_3$): δ 6.79 (q, J=7.1 Hz, 1H, E/Z isomers), 5.71-5.27 (m, 2H, E/Z isomers), 4.11-3.92 (m, 4H, E/Z isomers), 2.99 (d, J=5.4 Hz, 2H, Z isomer), 2.93 (d, J=5.1 Hz, 2H, E isomer), 2.31 (t, J=7.6 Hz, 2H, E/Z isomers), 2.16-1.90 (m, 2H, E/Z isomers), 1.73 (d, 3H, CHCH$_3$, Z isomer overlapped with the CHCH$_3$ signal of E isomer), 1.70 (d, J=7.2 Hz, 3H, CH$_3$, E isomer), 1.63-1.45 (m, 4H, E/Z isomers), 1.43-1.15 (m, 4H, E/Z isomers), 0.86 ppm (m, 6H, E/Z isomers).

$^{13}$C NMR (75 MHz, CDCl$_3$): δ 171.9, 171.8 (Z isomer), 167.6, 137.6 (Z isomer), 137.4, 133.5, 132.6, 132.5 (Z isomer), 132.0 (Z isomer), 122.3, 121.7 (Z isomer), 64.3, 64.1, 38.1, 32.8 (Z isomer), 31.8, 30.7, 30.6, 26.7 (Z isomer), 26.1, 26.0 (Z isomer), 19.2, 19.1, 14.2, 13.7, 13.6 ppm.

GCMS-EI m/z (%): 310 (M+, 1), 236 (7), 208 (6), 179 (11), 162 (100), 147 (8), 134 (50), 120 (11), 107 (22), 99 (13), 93 (12), 81 (13), 67 (5), 57 (27), 54 (26), 41 (39).

EI-HRMS calcd for C$_{18}$H$_{30}$O$_4$ [M]+: 310.21386; found: 310.21401.

Example 7

Effects of Ligands

Figure 5:
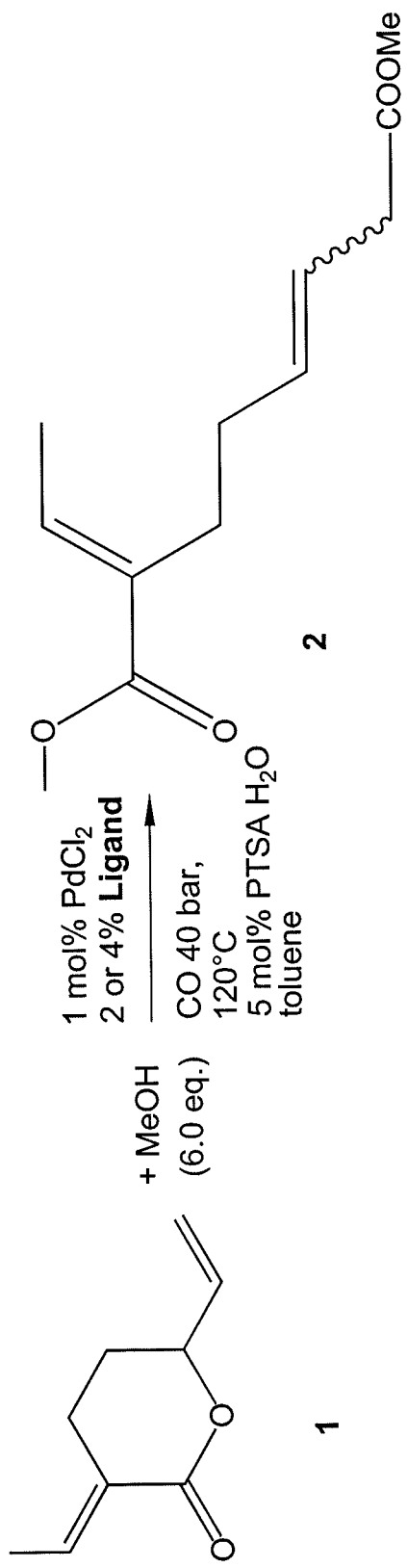
FIG. 5 is a reaction scheme used in experiments for determining the effect of a ligand attached to the palladium catalyst.
Figure 6A:
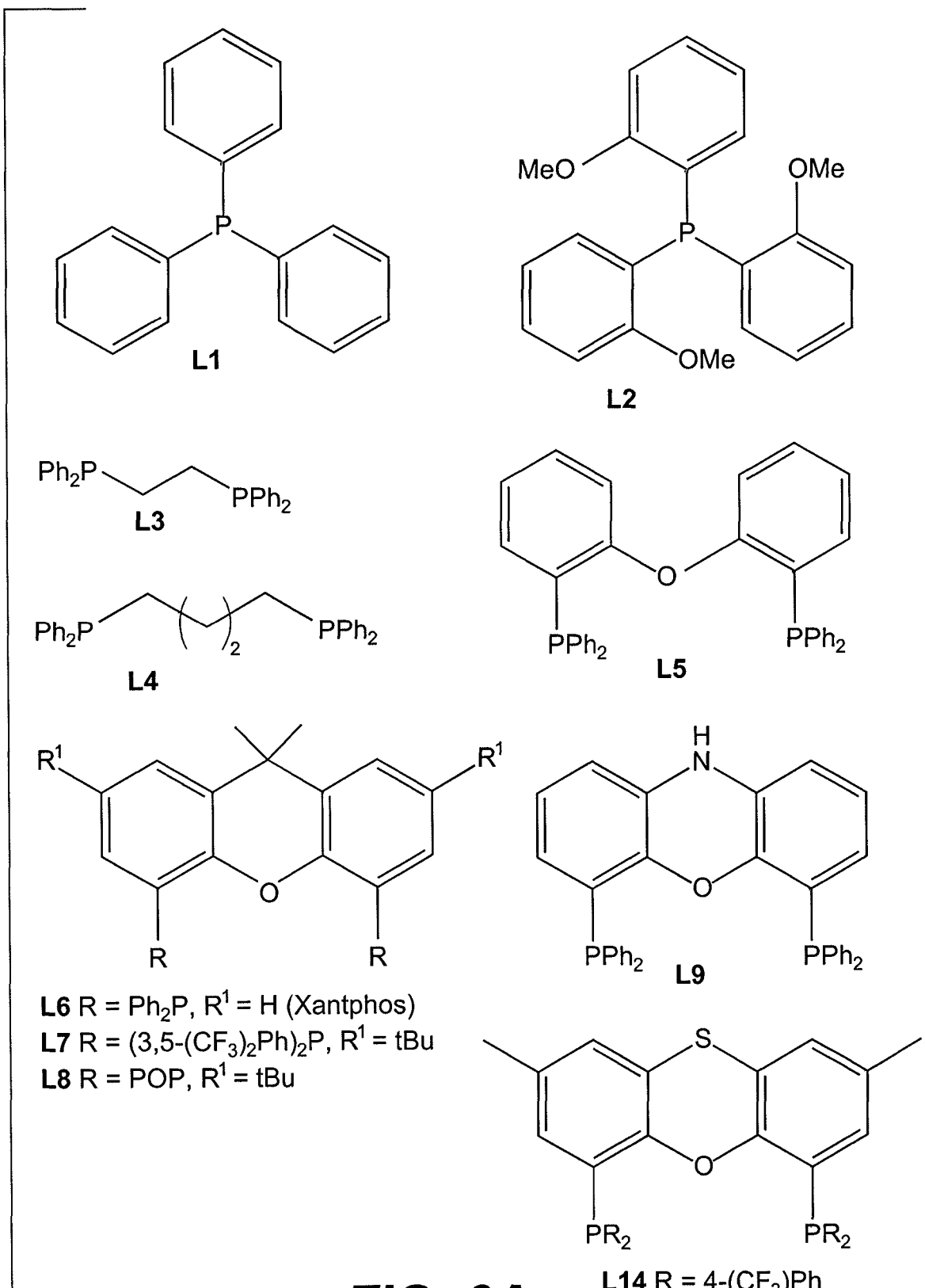
FIGS. 6A, 6B, and 6C show the ligands used in determining the effect of ligands in the reaction scheme of FIG. 5.
Figure 6B:
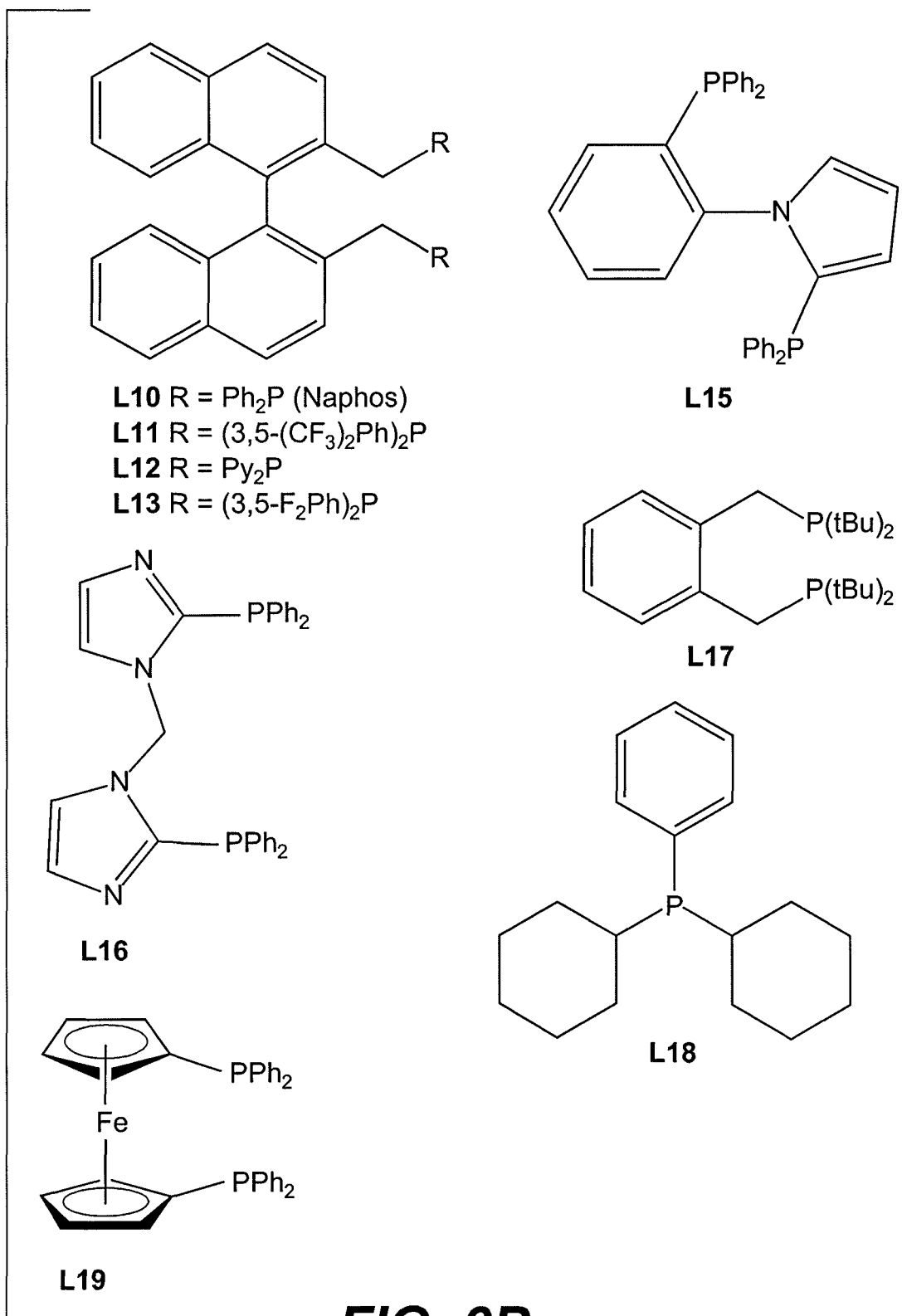
Figure 6C:
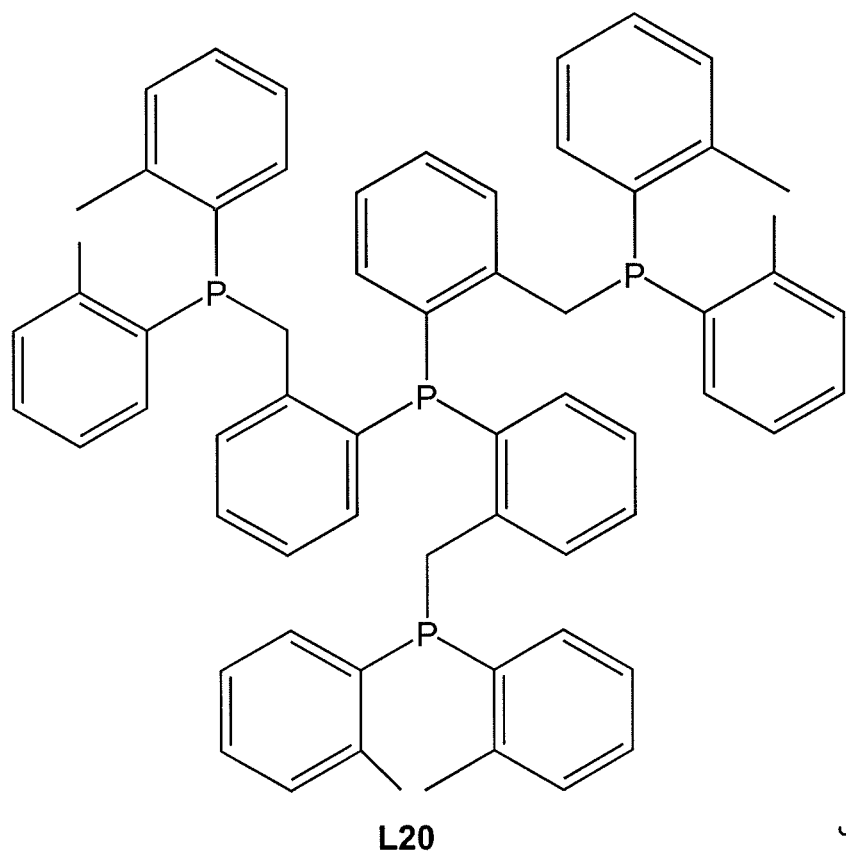
Figure 6C:
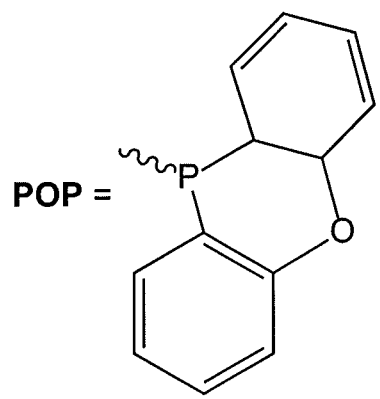
Figure 6C:
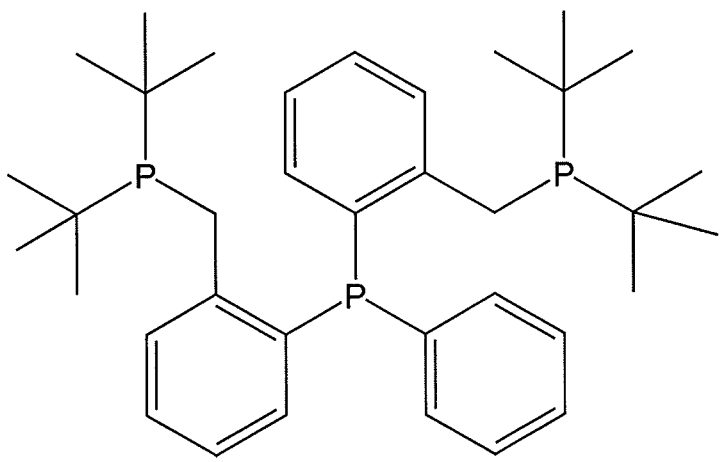

Examples 8-35 were conducted to determine the effects of ligands used during alkoxycarboxylation of the δ-lactone 1. FIG. 5 shows the reaction scheme used in determining the effects of the ligands, while FIGS. 6A-6C show the various ligands tested. Essentially, methyl alcohol was the primary alcohol used in all of the experiments in an effort to synthesize the dimethyl ester of formula 2. A summary of the yields and E/Z stereoisomer ratio of the diester products of formula 2 obtained for each ligand is shown in Table 4, below. The experimental procedure for each ligand is described in Examples 8-35.

TABLE 4

Effects of Ligands

| Example | Pd (mol %) | Ligand (mol %) | Reaction time (h) | Yield 2 (%) | E/Z ratio |
|---|---|---|---|---|---|
| 8 | PdCl$_2$ (1.0) | none | 5 | 29 | 4.2 |
| 9 | PdCl$_2$ (1.0) | none | 20 | 42 | 4.2 |
| 10 | PdCl$_2$ (1.0) | L1 (4.0 mol %) | 5 | 17 | 4.0 |
| 11 | PdCl$_2$ (1.0) | L1 (4.0 mol %) | 20 | 20 | 3.6 |
| 12 | PdCl$_2$ (1.0) | L2 (4.0 mol %) | 5 | 39 | 4.2 |
| 13 | PdCl$_2$ (1.0) | L3 (2.0 mol %) | 5 | trace | — |
| 14 | PdCl$_2$ (1.0) | L4 (2.0 mol %) | 5 | 13 | 4.4 |
| 15 | PdCl$_2$ (1.0) | L5 (2.0 mol %) | 5 | 3 | 3.7 |
| 16 | PdCl$_2$ (1.0) | L5 (2.0 mol %) | 20 | 19 | 3.7 |
| 17 | PdCl$_2$ (1.0) | L6 (2.0 mol %) | 5 | 56 | 3.4 |
| 18 | PdCl$_2$ (1.0) | L6 (2.0 mol %) | 20 | 10 | 0.8 |
| 19 | PdCl$_2$ (1.0) | L7 (2.0 mol %) | 5 | 75 | 3.8 |
| 20 | PdCl$_2$ (1.0) | L8 (2.0 mol %) | 5 | 16 | 2.0 |
| 21 | PdCl$_2$ (1.0) | L9 (2.0 mol %) | 5 | 44 | 4.1 |
| 22 | PdCl$_2$ (1.0) | L10 (2.0 mol %) | 5 | 32 | 4.1 |
| 23 | PdCl$_2$ (1.0) | L11 (2.0 mol %) | 5 | 83 | 3.8 |
| 24 | PdCl$_2$ (1.0) | L11 (2.0 mol %) | 20 | 85 | 3.7 |
| 25 | PdCl$_2$ (1.0) | L12 (2.0 mol %) | 5 | 8 | 4.4 |
| 26 | PdCl$_2$ (1.0) | L13 (2.0 mol %) | 5 | 78 | 3.2 |
| 27 | PdCl$_2$ (1.0) | L14 (2.0 mol %) | 5 | 1 | — |
| 28 | PdCl$_2$ (1.0) | L15 (2.0 mol %) | 5 | 0 | — |
| 29 | PdCl$_2$ (1.0) | L16 (2.0 mol %) | 5 | 2 | — |
| 30 | PdCl$_2$ (1.0) | L17 (2.0 mol %) | 5 | 9 | 1.3 |
| 31 | PdCl$_2$ (1.0) | L17 (2.0 mol %) | 20 | 2 | 0.8 |
| 32 | PdCl$_2$ (1.0) | L18 (4.0 mol %) | 20 | 3.5 | — |
| 33 | PdCl$_2$ (1.0) | L19 (2.0 mol %) | 5 | 3.8 | 4.4 |
| 34 | PdCl$_2$ (1.0) | L20 (2.0 mol %) | 5 | — | — |
| 35 | PdCl$_2$ (1.0) | L21 (2.0 mol %) | 5 | — | — |

Example 8

No Ligand—5 hr Reaction Time

A 4 mL vial was charged with PdCl$_2$ (1.7 mg, 1 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 9

No Ligand—20 hr Reaction Time

A 4 mL vial was charged with PdCl$_2$ (1.7 mg, 1 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA. H$_2$O solution in MeOH (0.25 mL, 5 mol %), were injected into the vial by syringe. The vial was placed in an alloy plate, which was transferred into an autoclave (300 mL) of the 4560 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 10

Ligand L1-5 hr Reaction Time

A 4 mL vial was charged with $PdCl_2$ (1.7 mg, 1 mol %), L1 (11.0 mg, 4 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 11

Ligand L1—20 hr Reaction Time

A 4 mL vial was charged with $PdCl_2$ (1.7 mg, 1 mol %), L1 (10.8 mg, 4 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 12

Ligand L2—5 hr Reaction Time

A 4 mL vial was charged with $PdCl_2$ (1.7 mg, 1 mol %), L2 (14.1 mg, 4 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 13

Ligand L3—5 hr Reaction Time

A 4 mL vial was charged with $PdCl_2$ (1.7 mg, 1 mol %), L3 (8.0 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 14

Ligand L4—5 hr Reaction Time

A 4 mL vial was charged with $PdCl_2$ (1.7 mg, 1.0 mol %), L4 (8.6 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 15

Ligand L5—5 hr Reaction Time

A 4 mL vial was charged with $PdCl_2$ (1.7 mg, 1 mol %), L5 (10.6 mg, 2 mol %), lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 16

Ligand L5—20 hr Reaction Time

A 4 mL vial was charged with $PdCl_2$ (1.7 mg, 1 mol %), L5 (10.6 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 17

Ligand L6—5 hr Reaction Time

A 4 mL vial was charged with $PdCl_2$ (1.7 mg, 1 mol %), L6 (11.7 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 18

Ligand L6—20 hr Reaction Time

A 4 mL vial was charged with $PdCl_2$ (1.7 mg, 1 mol %), L6 (11.7 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 19

Ligand L7—5 hr Reaction Time

A 4 mL vial was charged with $PdCl_2$ (1.7 mg, 1 mol %), L7 (24.6 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 20

Ligand L8—5 hr Reaction Time

A 4 mL vial was charged with $PdCl_2$ (1.7 mg, 1 mol %), L8 (14.2 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $PTSA.H_2O$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 21

Ligand L9—5 hr Reaction Time

A 4 mL vial was charged with $PdCl_2$ (1.7 mg, 1 mol %), L9 (11.2 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 22

Ligand L10—5 hr Reaction Time

A 4 mL vial was charged with PdCl$_2$ (1.7 mg, 1 mol %), L10 (12.9 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 23

Ligand L11—5 hr Reaction Time

A 4 mL vial was charged with PdCl$_2$ (1.7 mg, 1 mol %), L11 (23.5 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 24

Ligand L11—20 hr Reaction Time

A 4 mL vial was charged with PdCl$_2$ (1.7 mg, 1 mol %), L11 (23.5 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 25

Ligand L12—5 hr Reaction Time

A 4 mL vial was charged with PdCl$_2$ (1.7 mg, 1 mol %), L12 (12.9 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 26

Ligand L13—5 hr Reaction Time

A 4 mL vial was charged with PdCl$_2$ (1.7 mg, 1 mol %), L13 (15.6 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 27

Ligand L14—5 hr Reaction Time

A 4 mL vial was charged with PdCl$_2$ (1.7 mg, 1 mol %), L14 (17.2 mg, 2 mol %), δ-lactone 1 (152 mg, 1.0 mmol)

and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 28

Ligand L15—5 hr Reaction Time

A 4 mL vial was charged with PdCl$_2$ (1.7 mg, 1 mol %), L15 (10.7 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 29

Ligand L16—5 hr Reaction Time

A 4 mL vial was charged with PdCl$_2$ (1.7 mg, 1 mol %), L16 (10.4 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 30

Ligand L17—5 hr Reaction Time

A 4 mL vial was charged with PdCl$_2$ (1.7 mg, 1 mol %), L17 (7.8 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 31

Ligand L17—20 hr Reaction Time

A 4 mL vial was charged with PdCl$_2$ (1.7 mg, 1 mol %), L17 (7.8 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 32

Ligand L18—20 hr Reaction Time

A 4 mL vial was charged with PdCl$_2$ (1.7 mg, 1 mol %), L18 (11.0 mg, 4 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 20 h at 120° C. After the reaction finished, the autoclave was cooled to room temperature and the pressure was carefully released. Then hexadecane (0.100 mL) was injected as the internal standard. Yield and selectivity were measured by GC analysis.

Example 33

Ligand L19—5 hr Reaction Time

A 4 mL vial was charged with PdCl$_2$ (1.7 mg, 1 mol %), L19 (11.1 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 34

Ligand L20—5 hr Reaction Time

A 4 mL vial was charged with PdCl$_2$ (1.7 mg, 1 mol %), L20 (18.8 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 35

Ligand L21—5 hr Reaction Time

A 4 mL vial was charged with PdCl$_2$ (1.7 mg, 1 mol %), L21 (11.6 mg, 2 mol %), δ-lactone 1 (152 mg, 1.0 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M PTSA.H$_2$O solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 36

Effects of Acids

Figure 7:
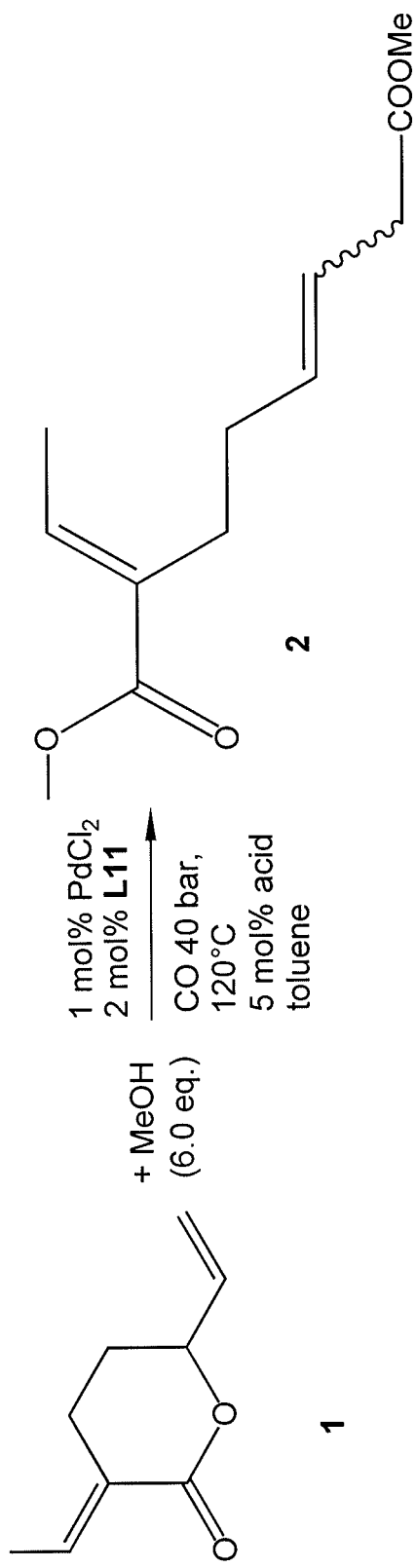
FIG. 7 shows the reaction scheme used in determining the effect of the acid in the reaction scheme of FIG. 1.

Examples 37-39 were conducted to determine the effects of the acid promoter used during synthesis. FIG. 7 shows the reaction scheme used in determining the effects of the acid. A summary of the yields and E/Z stereoisomer ratio of the diester products of formula 2 obtained for each ligand is shown in Table 5, below. The experimental procedure for each ligand is described in Examples 37-39.

TABLE 5

Effects of Acid

| Example | Acid (mol %) | Yield 2 (%) | E/Z ratio |
|---------|--------------|-------------|-----------|
| 37 | CH$_3$SO$_3$H (5.0) | 84 | 3.9 |
| 38 | HCl (5.0) | 33 | 3.7 |
| 39 | H$_2$SO$_4$ (5.0) | 89 | 4.1 |

Example 37

Methanesulfonic Acid

A 4 mL vial was charged with PdCl$_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M methanesulfonic acid (CH$_3$SO$_3$H) solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 38

Hydrochloric Acid

A 4 mL vial was charged with PdCl$_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), HCl (2M in diethylether) (0.025 mL, 5.0 mol %) and MeOH (0.25 mL), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 39

Sulfuric Acid

A 4 mL vial was charged with PdCl$_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 40

Effect of Solvent

Figure 8:
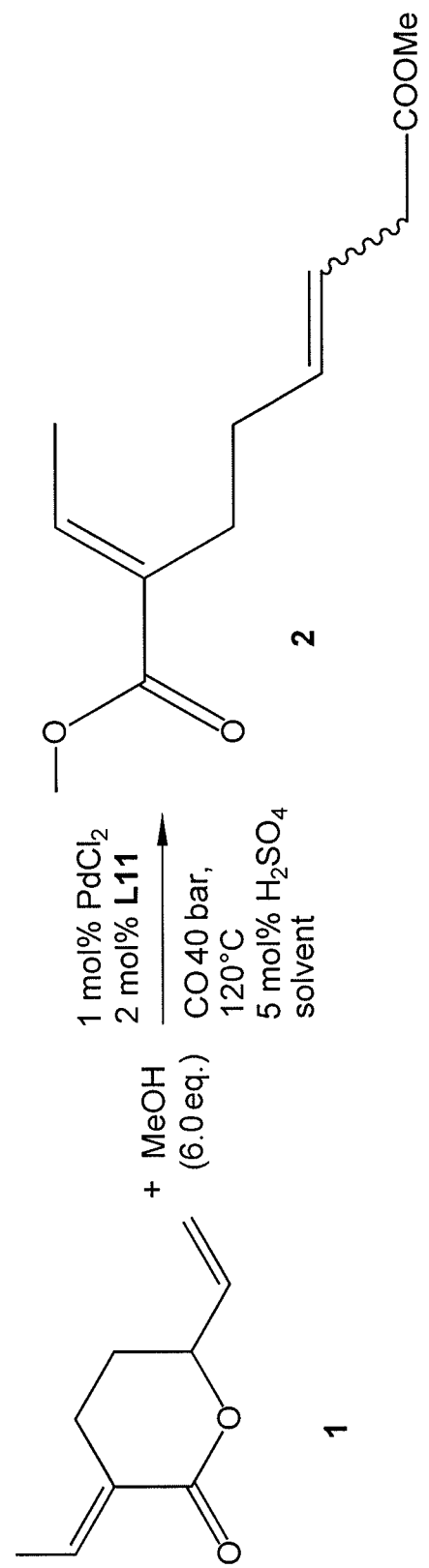
FIG. 8 shows the reaction scheme used in determining the effect of the solvent in the reaction scheme of FIG. 1.

Examples 41-43 were conducted to determine the effects of solvents used during synthesis on the yield of compound 2. FIG. 8 shows the scheme used in determining the effect of the solvent. The effects of the various solvents are summarized in Table 6, shown below.

TABLE 6

Effect of Solvent

| Example | Solvent | Yield 2 (%) | E/Z ratio |
|---|---|---|---|
| 41 | $CH_3CN$ | 37 | 4.0 |
| 42 | MeOH | 45 | 3.8 |
| 43 | THF | 39 | 4.2 |

Example 41

Acetonitrile

A 4 mL vial was charged with $PdCl_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. $CH_3CN$ (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 42

Methyl Alcohol

A 4 mL vial was charged with $PdCl_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. MeOH (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 43

Tetrahydrofuran

A 4 mL vial was charged with $PdCl_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. THF (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 44

Effect of Palladium Precursor

Figure 9:
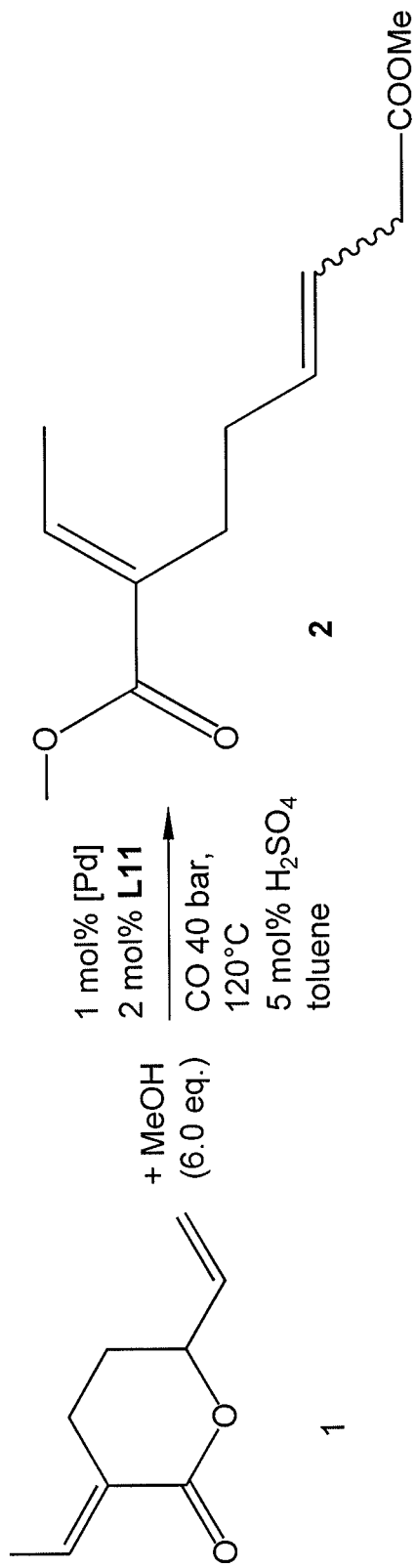
FIG. 9 shows the reaction scheme used in determining the effect of the palladium precursor in the reaction scheme of FIG. 1.

Examples 45-47 were conducted to determine the effects of the palladium precursor used during synthesis on the yield of compound 2. FIG. 9 shows the scheme used in determining the effects of the palladium precursor. The effects of the various precursors are summarized in Table 7, shown below.

TABLE 7

Effect of Palladium Precursor

| Example | Pd Precursor (mol %) | Yield 2 (%) | E/Z ratio |
|---|---|---|---|
| 45 | $PdCl_2(CH_3CN)_2$ (1.0) | 88 | 4.0 |
| 46 | $Pd(dba)_2$ (1.0) | 16 | 3.8 |
| 47 | $Pd(OAc)_2$ (1.0) | 19 | 3.7 |

Example 45

Bis(acetonitrile)Dichloropalladium(II)

A 4 mL vial was charged with $PdCl_2(CH_3CN)_2$ (2.6 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber)

and phenolic cap. The vial was then connected to the atmosphere with a needle. The vial was evacuated and refilled with argon three times. Toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 46

Bis(dibenzylideneacetone)Palladium(0)

A 4 mL vial was charged with $Pd(dba)_2$ (5.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 47

Palladium Acetate

A 4 mL vial was charged with $Pd(OAc)_2$ (2.3 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 48

Effect of Acid and Methanol Amounts

Figure 10:
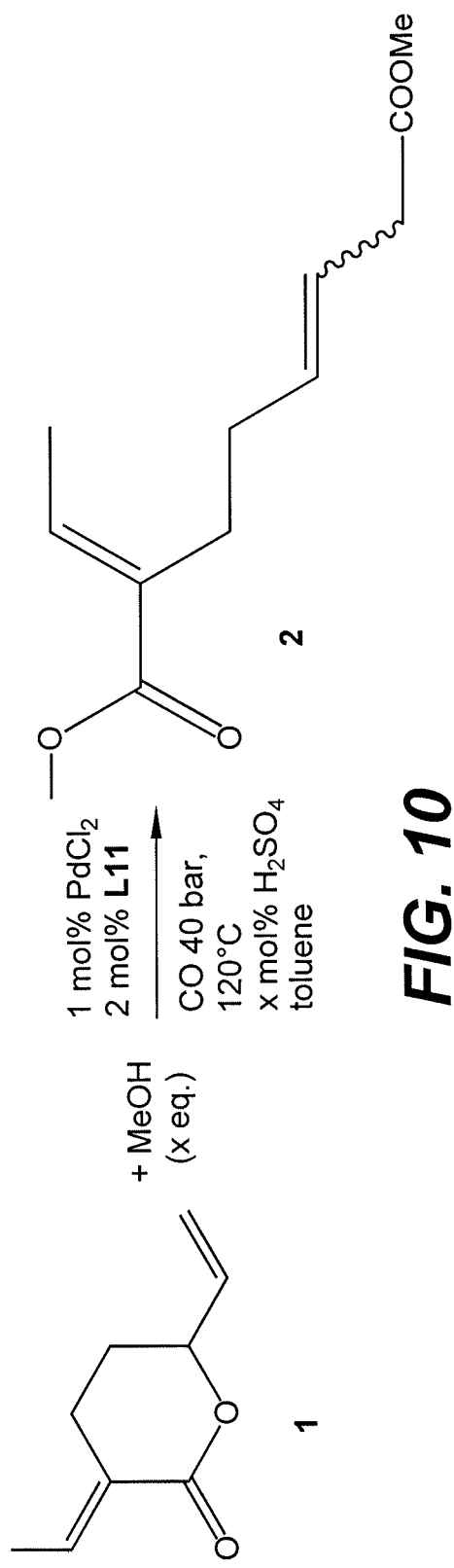
FIG. 10 shows the reaction scheme used in determining the effect of the acid and methanol amounts in the reaction scheme of FIG. 1.

Examples 49-56 were conducted to determine the effect of the acid and methanol amounts used during synthesis on the yield of compound 2. FIG. 10 shows the scheme used in determining the effects of the acid and methanol amounts. The effects are summarized in Table 8, shown below.

TABLE 8

Effect of Acid and Methanol Amounts

| Example | mL MeOH | Acid (mol %) | Yield 2 (%) | E/Z ratio |
|---|---|---|---|---|
| 49 | 0.25 (6.0 eq) | PTSA•$H_2O$ (1.0) | 58 | 4.0 |
| 50 | 0.25 (6.0 eq) | PTSA•$H_2O$ (10.0) | 89 | 4.1 |
| 51 | 0.08 (2.0 eq) | PTSA•$H_2O$ (15.0) | 55 | 2.6 |
| 52 | 0.12 (3.0 eq) | PTSA•$H_2O$ (15.0) | 81 | 3.6 |
| 53 | 0.25 (6.0 eq) | PTSA•$H_2O$ (15.0) | 90 | 4.0 |
| 54 | 0.25 (6.0 eq) | PTSA•$H_2O$ (21.0) | 92 | 4.1 |
| 55 | 0.25 (6.0 eq) | $H_2SO_4$ (7.5) | 91 | 4.1 |
| 56 | 0.50 (12.0 eq) | $H_2SO_4$ (5.0) | 91 | 4.2 |

Example 49

MeOH (6.0 eq.)/PTSA 1.0 mol. %

A 4 mL vial was charged with $PdCl_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), 0.2 M PTSA.$H_2O$ solution in MeOH (0.050 mL, 1 mol %) and MeOH (0.20 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 50

MeOH 6.0 eq./PTSA 10.0 mol. %

A 4 mL vial was charged with $PdCl_2$ (1.7 mg, 1 mol %), δ-lactone 1 (152 mg, 1.0 mmol), L11 (23.5 mg, 2 mol %), PTSA.$H_2O$ (19.0 mg, 10 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), and MeOH (0.25 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 51

MeOH 2.0 eq./PTSA 15 mol. %

A 4 mL vial was charged with $PdCl_2$ (1.7 mg, 1 mol %), δ-lactone 1 (152 mg, 1.0 mmol), L11 (23.5 mg, 2 mol %), PTSA.H$_2$O (28.4 mg, 15 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), and MeOH (0.08 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 52

MeOH 3.0 eq./PTSA 15 mol. %

A 4 mL vial was charged with PdCl$_2$ (1.7 mg, 1 mol %), δ-lactone 1 (152 mg, 1.0 mmol), L11 (23.5 mg, 2 mol %), PTSA.H$_2$O (28.4 mg, 15 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), and MeOH (0.12 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 53

MeOH 6.0 eq./PTSA 15 mol. %

A 4 mL vial was charged with PdCl$_2$ (1.7 mg, 1 mol %), δ-lactone 1 (152 mg, 1.0 mmol), L11 (23.5 mg, 2 mol %), PTSA.H$_2$O (28.4 mg, 15 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), and MeOH (0.25 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 54

MeOH 6.0 eq./PTSA 21 mol. %

A 4 mL vial was charged with PdCl$_2$ (1.7 mg, 1 mol %), δ-lactone 1 (152 mg, 1.0 mmol), L11 (23.5 mg, 2 mol %), PTSA.H$_2$O (40.0 mg, 21 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and MeOH (0.25 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 55

MeOH 6.0 eq./H$_2$SO$_4$ 7.5 mol. %

A 4 mL vial was charged with PdCl$_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL) and 0.3 M H$_2$SO$_4$ solution in MeOH (0.250 mL, 7.5 mol %) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was carefully released. Then hexadecane (0.100 mL) was injected as the internal standard. Yield and selectivity were measured by GC analysis.

Example 56

MeOH 12.0 eq./H$_2$SO$_4$ 5.0 mol. %

A 4 mL vial was charged with PdCl$_2$ (1.7 mg, 1 mol %), δ-lactone 1 (152 mg, 1.0 mmol), L11 (23.5 mg, 2 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. Toluene (2.0 mL), 0.2 M H$_2$SO$_4$ solution in MeOH (0.250 mL, 5 mol %) and MeOH (0.25 35 mL) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 57

Effects of Pressure

Figure 11:
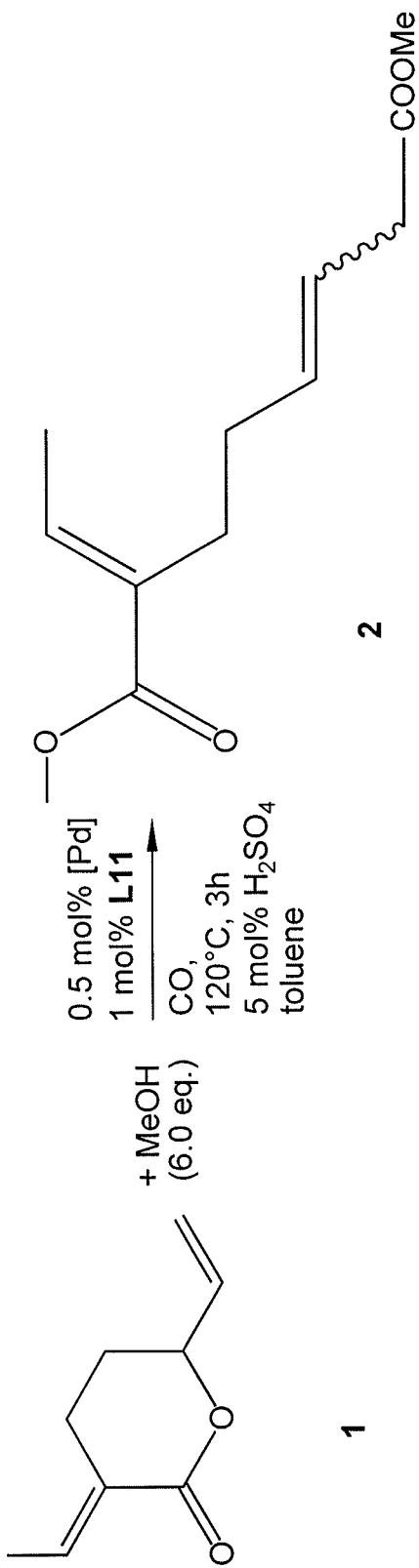
FIG. 11 shows the reaction scheme used in determining the effect of the pressure in the reaction scheme of FIG. 1.

Examples 58-61 were conducted to determine the effects of pressure used during synthesis of compound 2. FIG. 11 shows the scheme used in determining the effects of pressure. The effects of pressure are summarized in Table 9 shown below.

TABLE 9

Effect of Pressure

| Example | Acid (mol %) | $P_{CO}$ (bar) | Yield 2 (%) | E/Z ratio |
|---|---|---|---|---|
| 58 | $H_2SO_4$ (5 mol %) | 50 | 89 | 4.0 |
| 59 | $H_2SO_4$ (5 mol %) | 40 | 89 | 4.0 |
| 60 | $H_2SO_4$ (5 mol %) | 30 | 89 | 4.0 |
| 61 | $H_2SO_4$ (5 mol %) | 20 | 87 | 3.9 |

Example 58

50 Bar Pressure

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of $PdCl_2$ (0.85 mg, 0.5 mol %) and L11 (11.9 mg, 1 mol %) in toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 50 bar at room temperature. The reaction was performed for 3 h at 120° C. After the reaction finished, the autoclave was cooled to room temperature and the pressure was carefully released. Then hexadecane (0.100 mL) was injected as the internal standard. Yield and selectivity were measured by GC analysis.

Example 59

40 Bar Pressure

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of $PdCl_2$ (0.85 mg, 0.5 mol %) and L11 (11.9 mg, 1 mol %) in toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 3 h at 120° C. After the reaction finished, the autoclave was cooled to room temperature and the pressure was carefully released. Then hexadecane (0.100 mL) was injected as the internal standard. Yield and selectivity were measured by GC analysis.

Example 60

30 Bar Pressure

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of $PdCl_2$ (0.85 mg, 0.5 mol %) and L11 (11.9 mg, 1 mol %) in toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 3 h at 120° C. After the reaction finished, the autoclave was cooled to room temperature and the pressure was carefully released. Then hexadecane (0.100 mL) was injected as the internal standard. Yield and selectivity were measured by GC analysis.

Example 61

20 Bar Pressure

A 4 mL vial was charged δ-lactone 1 (152 mg, 1.0 mmol), and a magnetic stirring bar. The 40 vial was then sealed with Septa (PTFE-faced styrene-butadiene rubber) and phenolic cap. The vial was then connected to the atmosphere with a needle. The vial was evacuated and refilled with argon three times. A solution of $PdCl_2$ (0.85 mg, 0.5 mol %) and L11 (11.9 mg, 1 mol %) in toluene (2.0 mL) and 0.2 M $H_2SO_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 20 bar at room temperature. The reaction was performed for 3 h at 120° C. After the reaction finished, the autoclave was cooled to room temperature and the pressure was carefully released. Then hexadecane (0.100 mL) was injected as the internal standard. Yield and selectivity were measured by GC analysis.

Example 62

Effect of Temperature

Figure 12:
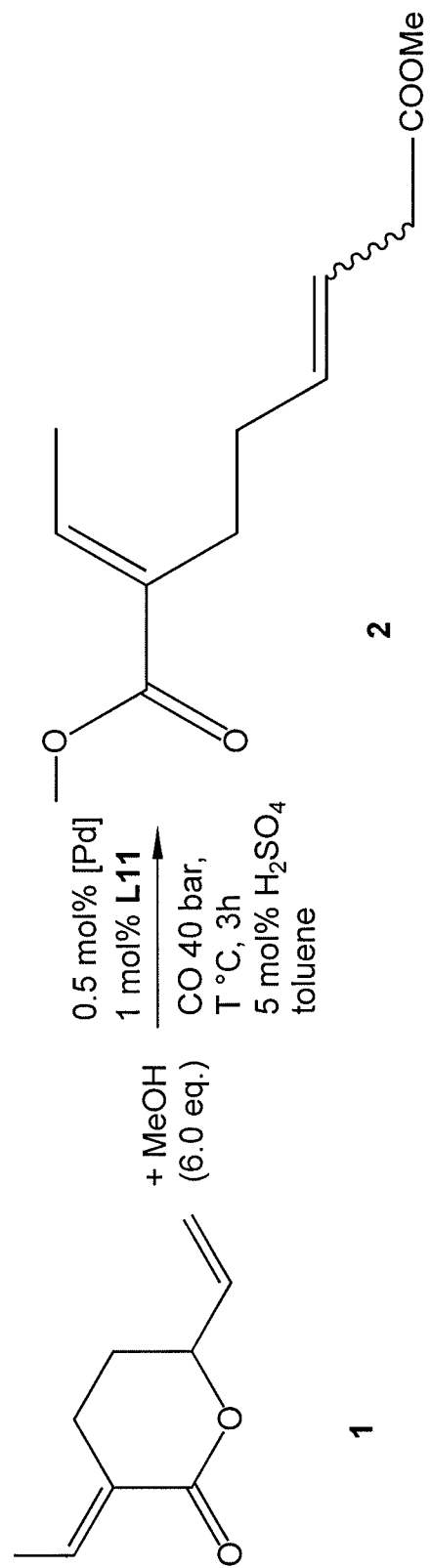
FIG. 12 shows the reaction scheme used in determining the effect of the temperature in the reaction scheme of FIG. 1.

Examples 63-65 were conducted to determine the effect of temperature used during synthesis on yield of compound 2. FIG. 12 shows the scheme used in determining the effect of temperature. The effect of temperature is summarized in Table 10, shown below.

TABLE 10

Effect of Temperature

| Example | Acid (mol %) | T (° C.) | Yield 2 (%) | E/Z ratio |
|---|---|---|---|---|
| 63 | $H_2SO_4$ (5 mol %) | 130 | 86 | 4.0 |
| 64 | $H_2SO_4$ (5 mol %) | 120 | 89 | 4.0 |
| 65 | $H_2SO_4$ (5 mol %) | 110 | 87 | 4.1 |

Example 63

Temp 130° C.

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.2 M H$_2$SO$_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 3 h at 130° C. After the reaction finished, the autoclave was cooled to room temperature and the pressure was carefully released. Then hexadecane (0.100 mL) was injected as the internal standard. Yield and selectivity were measured by GC analysis.

Example 64

Temp 120° C.

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.2 M H$_2$SO$_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 3 h at 120° C. After the reaction finished, the autoclave was cooled to room temperature and the pressure was carefully released. Then hexadecane (0.100 mL) was injected as the internal standard. Yield and selectivity were measured by GC analysis.

Example 65

Temp 110° C.

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.2 M H$_2$SO$_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 40 bar at room temperature. The reaction was performed for 3 h at 110° C. After the reaction finished, the autoclave was cooled to room temperature and the pressure was carefully released. Then hexadecane (0.100 mL) was injected as the internal standard. Yield and selectivity were measured by GC analysis.

Example 66

Alcohol Scope

Figure 13:
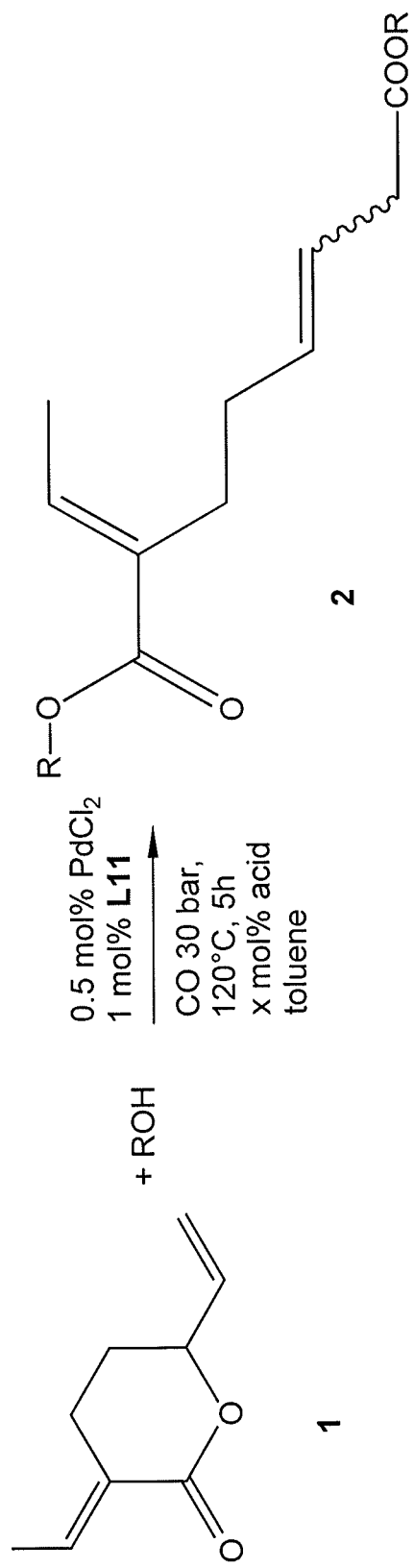
FIG. 13 shows the reaction scheme used in determining the effect of the alcohol scope in the reaction scheme of FIG. 1.

Examples 67-73 were conducted to determine the scope of alcohol during synthesis. FIG. 13 shows the scheme used in determining the scope of alcohol. The results are summarized in Table 11, shown below.

TABLE 11

Scope of Alcohol

| Example | Alcohol | Acid (mol %) | Yield 2 (%) | E/Z ratio |
|---|---|---|---|---|
| 67 | MeOH (6.0 equiv.) | H$_2$SO$_4$ (5 mol %) | 90 | 4.3 |
| 68 | nBuOH (6.0 equiv.) | H$_2$SO$_4$ (5 mol %) | 90 | 3.8 |
| 69 | 2-Ethylhexanol (6.0 equiv.) | H$_2$SO$_4$ (5 mol %) | 99 | 4.2 |
| 70 | iPrOH (6.0 equiv.) | H$_2$SO$_4$ (5 mol %) | 64 | 2.3 |
| 71 | tBuOH (6.0 equiv.) | PTSA·H$_2$O (10 mol %) | — | |
| 72 | PhCH$_2$OH (6.0 equiv.) | PTSA·H$_2$O (10 mol %) | 73 | 4.5 |
| 73 | PhOH (6.0 equiv.) | PTSA·H$_2$O (10 mol %) | — | |

Example 67

MeOH (6 eq.)/H$_2$SO$_4$ (5 mol %)

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.2 M H$_2$SO$_4$ solution in MeOH (0.25 mL, 5 mol %), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. Then hexadecane (0.100 mL) was injected as the internal standard. Yield and selectivity were measured by GC analysis.

Example 68 n-Butanol/H$_2$SO$_4$ (5 mol %)

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.096 M H$_2$SO$_4$ solution in n-butanol (0.55 mL, 6 mmol) were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The isomeric ratio was measured by GC analysis. Isolated yield.

Example 69

2-Ethylhexanol/H$_2$SO$_4$ (5 mol %)

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.053 M H$_2$SO$_4$ solution in 2-ethylhexanol (0.94 mL, 6 mmol), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The isomeric ratio was measured by GC analysis. Isolated yield.

Example 70 i-Propanol/H$_2$SO$_4$ (5 mol %)

A 4 mL vial was charged δ-lactone 1 (152 mg, 1.0 mmol), and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and 0.109 M H$_2$SO$_4$ solution in i-propanol (0.46 mL, 6 mmol), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The isomeric ratio was measured by GC analysis. Isolated yield.

Example 71 t-Butanol/PTSA (10 mol %)

A 4 mL vial was charged δ-lactone 1 (152 mg, 1.0 mmol), PTSA.H$_2$O (19.0 mg, 10 mol %), t-butanol (450 mg, 6 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) was injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The diester was not detected by GC-MS analysis.

Example 72

Benzyl Alcohol/PTSA (10 mol %)

A 4 mL vial was charged δ-lactone 1 (152 mg, 1.0 mmol), PTSA.H$_2$O (19.0 mg, 10 mol %) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) and benzyl alcohol (0.62 mL, 6 mmol), were injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The isomeric ratio was measured by GC analysis. Isolated yield.

Example 73

Phenol/PTSA (10 mol %)

A 4 mL vial was charged δ-lactone 1 (152 mg, 1.0 mmol), PTSA.H$_2$O (19.0 mg, 10 mol %), phenol (565 mg, 6 mmol) and a magnetic stirring bar. The vial was then sealed with Septa (PTFE-faced styrene-butadiene rubber) and phenolic cap. The vial was then connected to the atmosphere with a needle. The vial was evacuated and refilled with argon three times. A solution of PdCl$_2$ (0.85 mg, 0.5 mol %) and L11 (11.9 mg, 1 mol %) in toluene (2.0 mL) was injected into the vial by syringe. The vial was placed in an alloy plate, which was transferred into an autoclave (300 mL) of the 4760 series from Parr Instruments under argon atmosphere. After flushing the autoclave three times with CO, the pressure of CO was increased to 30 bar at room temperature. The reaction was performed for 5 h at 120° C. After the reaction finished, the autoclave was cooled to room temperature and the pressure was carefully released. The diester was not detected by GC-MS analysis.

The unsaturated esters obtained by the alkoxycarbonylation of 1 are valuable platform chemicals themselves. However, the corresponding saturated esters and the resulting diols are also of interest for applications. In order to transform 2 into saturated esters or diols, the metal-catalyzed alkoxycarbonylation of a lactone was extended by performing catalytic hydrogenations.

At first, commercial Pd/C (10 wt %) was used as the catalyst to hydrogenate the unsaturated diester 2a. See FIG. 14. Mild reaction conditions (10 bar H$_2$, 60° C.), previously reported by Behr and coworkers for the reduction of lactone 1 to 3,6-diethyltetrahydro-2H-pyran-2-one were used. We noticed a marked solvent effect on the chemoselectivity of the hydrogenation. When the reaction was performed in toluene, reduction of the di-substituted double bond was attained within 3 hours. However, the conjugated tri-substituted double bond was not reduced, even after 16 h. Complete reduction of the olefinic bonds of 2a to yield 4 was instead accomplished in 2.5 h using THF as the solvent (see FIG. 15). The latter diester 4 is of potential industrial interest for plasticizer applications and as a co-monomer in combination with diamines and diols to yield, respectively, polyamides and polyesters. On the other hand, the presence of a single unsaturation makes 3 comparable to 1,3-unsaturated esters, e.g., acrylic and tiglic acid derivatives, which are of interest for the preparation of different functional materials.

Example 74

Synthesis of dimethyl 2-ethyloctanedioate (Compound 4)

Pd/C 10 wt % (3.1 mg), compound 2a (1.4 mmol) and a magnetic stirring bar were added to a 4 mL vial. The vial was then sealed, connected to the atmosphere with a needle, and evacuated and refilled with argon three times. THF (3 mL) was added, and the vial placed inside a 300 mL stainless steel Parr autoclave. The autoclave was flushed three times with nitrogen, pressurized with hydrogen to 10 bar, and then heated to 60° C. for 2.5 h. The autoclave was cooled with an ice bath and vented. The reaction mixture was filtered through Celite, and the solvent evaporated, affording pure 4 as a colorless liquid in >99% yield): $^1$H NMR (300 MHz, CDCl$_3$) δ 3.61 (s, 3H), 3.60 (s, 3H), 2.32-2.14 (m, 3H), 1.49 (m, 6H), 1.32-1.12 (m, 4H), 0.82 ppm (t, J=7.4 Hz, 3H). $^{13}$C NMR (75 MHz, CDCl$_3$) δ 176.7, 174.1, 51.5, 51.3, 47.2, 34.0, 31.9, 29.1, 27.1, 25.5, 24.8, 11.8 ppm. GCMS-EI m/z (%)=199 (8), 171 (25), 166 (34), 157 (13), 138 (29), 129 (22), 114 (11), 102 (97), 97 (45), 87 (100), 69 (56), 59 (93), 55 (97), 41 (57). ESI-HRMS calcd for C$_{12}$H$_{22}$O$_4$Na [M+Na]+: 253.14103; found: 253.14109.

Figure 16:
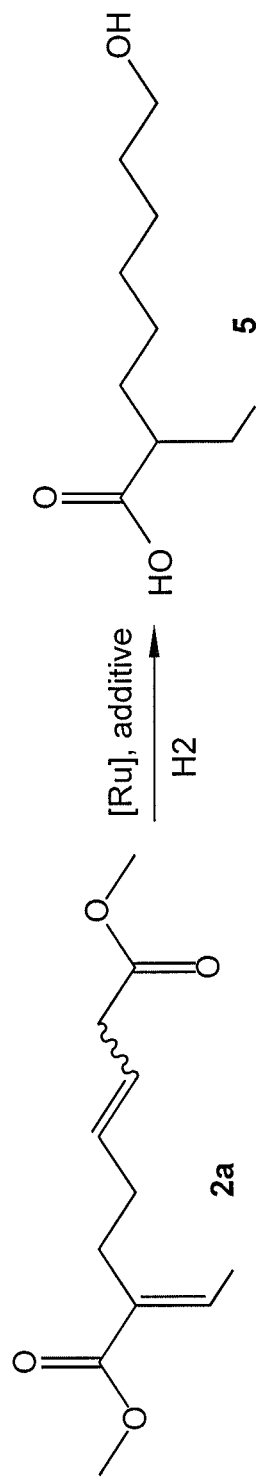
FIG. 16 is a third reaction scheme for further hydrogenating the diester obtained from the reaction scheme of FIG. 4, resulting in formation of a diol.
Figure 17:
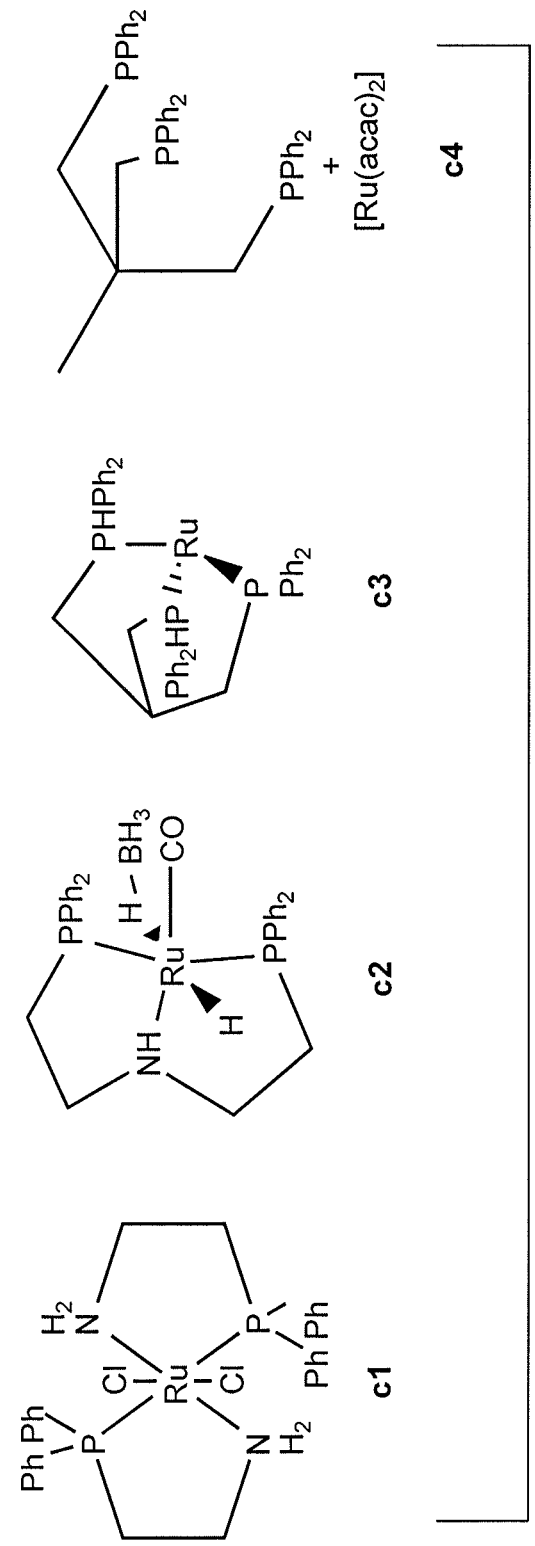
FIG. 17 is the structural formulas of various ruthenium additives tested in the reaction scheme of FIG. 16.

To further illustrate the versatility of 2 as a building block for polymers, we studied its hydrogenation to diol 5 (see FIGS. 16-17). The synthesis of 5 can be performed by the reduction of 4 using LiAlH$_4$ as the stoichiometric reagent, a classical method used in laboratory organic synthesis. However, when we performed this reaction, we found that the separation and purification of 5 from byproducts was difficult. Such a methodology is clearly not environmentally acceptable and not applicable to bulk scale industrial production. Thus, catalytic hydrogenation was investigated.

Ester and carboxylic acid moieties are challenging functional groups for hydrogenation reactions. In industrial processes, their hydrogenation is generally performed over heterogeneous catalysts at high pressures and temperatures. However, recently homogenously catalyzed hydrogenation of carboxylic acid derivatives has experienced significant developments.

Hence, we applied two different commercially available ruthenium based catalysts to the reduction of 2a to 5, including a Noyori-type ruthenium catalyst first reported by Saudan et al. for the hydrogenation of esters (catalyst c1, FIG. 17) and the tetrahydro-borato form of the ruthenium PNP pincer complex named Ru-MACHO™ (catalyst c2, FIG. 17) discovered by Kuriyama and coworkers at Takasago company. In both cases, reaction conditions commonly used for these catalytic systems were employed (Table 12, below, entries 1 and 2). Unfortunately, even after 22 h only traces of diol were present using c1 as the catalyst, and just 8% yield was obtained using c2. Promising results were instead obtained using ruthenium complexes of 1,1,1-tris-(diphenylphosphinomethyl)ethane (Triphos). Here, we started our investigation using both c4 (ruthenium acetylacetonate/Triphos) in combination with MSA in methanol (entry 3, Table 12) and c3 in THF in the absence of any additive (entry 4, Table 12). The first system yielded 35% of diol 5, while the latter afforded mainly a mixture of the esters 3 and 4. Encouraged by the result obtained with MSA, we tested sodium methoxide and bis(trifluoromethane)sulfonimide (HNTf$_2$) as additives. The use of HNTf$_2$ (10 mol %) afforded 69% yield of 5 (entry 5, Table 12). Finally, the desired full reduction of 2a to diol 5 was obtained under relatively mild conditions in 91% yield (80% isolated) upon reduction of the amount of HNTf$_2$ to 5 mol % and addition of 5 mol % of metallic zinc (entry 7, Table 12).

TABLE 12

Hydrogenation of diester 2a to diol 5

| Entry | Catalyst | Solvent | Additive (mol %) | CO (bar) | T (° C.) | t (h) | 5 Yield (%) |
|---|---|---|---|---|---|---|---|
| 1 | c1 | THF | MeONa (10) | 50 | 120 | 22 | traces |
| 2 | c2 | THF | — | 50 | 120 | 22 | 8 |
| 3 | c3 | THF | — | 70 | 150 | 22 | 2 |
| 4 | c4 | MeOH | MSA (10) | 70 | 150 | 22 | 35 |
| 5 | c4 | MeOH | HNTf$_2$ (10) | 70 | 150 | 22 | 69 |
| 6 | c4 | MeOH | MSA(5)/Zn(5) | 70 | 150 | 24 | 42 |
| 7 | c4 | MeOH | HNTf$_2$(5)/Zn(5) | 70 | 150 | 24 | 91 |
| 8 | c4 | MeOH | MeONa | 70 | 150 | 22 | 17 |
| 9 | c4 | dioxane | HNTf$_2$(5) | 70 | 150 | 22 | 24 |

Reaction conditions: 2a (0.5 mmol), metal complex (0.01 mmol), ligand when added (0.02 mmol), solvent (2 mL). Conversion of 2a was complete in all cases. Yields were determined by GC analysis using hexadecane as the internal standard.

Example 75

Synthesis of 2-ethyloctane-1,8-diol, Compound 5

[Ru(acac)$_3$] (4.0 mg, 0.01 mmol), Triphos (12.5 mg, 0.02 mmol) and zinc (1.6 mg, 2.5×10$^{-2}$ mmol) were weighed in a 4 mL vial in air. The vial was then sealed, connected to the atmosphere with a needle and evacuated and refilled with argon three times. Compound 2a (0.5 mmol) and 2 mL of a stock solution of HNTf$_2$ (7.0 mg, 2.5×10$^{-2}$ mmol) in methanol were added. The vial was placed inside a 300 mL stainless steel Parr autoclave, and the autoclave was flushed three times with nitrogen, pressurized with hydrogen and heated. After 24 h, the autoclave was cooled with ice water and vented. The crude mixture was analyzed by gas chromatography. The product was purified by column chromatography on silica gel (gradient elution from CH$_2$Cl$_2$ to CH$_2$Cl$_2$/MeOH 9:1). $^1$H NMR (300 MHz, CDCl$_3$) δ 3.63 (t, J=6.6 Hz, 2H), 3.53 (d, J=5.0 Hz, 2H), 2.42 (br s, 2H), 1.70-1.47 (m, 2H), 1.44-1.15 (m, 11H), 0.88 ppm (t, J=7.3 Hz, 3H). $^{13}$C NMR (75 MHz, CDCl$_3$) δ 65.0, 62.7, 41.9, 32.7, 30.3, 29.8, 26.8, 25.7, 23.3, 11.1. GCMS-EI m/z (%)=172 (M+, 0.3), 144 (2), 126 (16), 109 (24), 97 (52), 83 (61), 69 (88), 55 (100). ESI-HRMS calcd for C10H23O2 [M+H]$^+$: 175.16926; found: 175.16928.

It is to be understood that the metal-catalyzed alkoxycarbonylation of lactone is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for metal-catalyzed alkoxycarbonylation of a δ-lactone, the δ-lactone being 3-ethylidene-6-vinyltetrahydro-2H-pyran-2-one, the method comprising the steps of:

adding an alcohol and a catalyst system including palladium or a salt thereof to a solution of the δ-lactone in an organic solvent to form a reaction mixture, wherein the catalyst system further comprises a phosphine ligand having the formula:

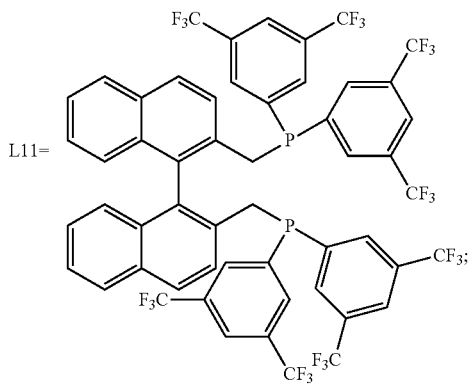 [SMILES: FC(F)(F)c1cc(P(Cc2ccc3ccccc3c2-c2c(CP(c3cc(C(F)(F)F)cc(C(F)(F)F)c3)c3cc(C(F)(F)F)cc(C(F)(F)F)c3)ccc3ccccc23)c2cc(C(F)(F)F)cc(C(F)(F)F)c2)cc(C(F)(F)F)c1]

placing the reaction mixture under pressure of carbon monoxide (CO) gas;
heating the reaction mixture to a temperature of at least 110° C.; and
recovering a 2-octendioate diester product.

2. The method for metal-catalyzed alkoxycarbonylation according to claim 1, further comprising a step of adding an acid to the reaction mixture.

3. The method for metal-catalyzed alkoxycarbonylation according to claim 2, wherein the acid is selected from the group consisting of p-toluenesulfonic acid, methanesulfonic acid, hydrochloric acid, and sulfuric acid.

4. The method for metal-catalyzed alkoxycarbonylation according to claim 2, wherein the acid is p-toluenesulfonic acid.

5. The method for metal-catalyzed alkoxycarbonylation according to claim 2, wherein the acid is sulfuric acid.

6. The method for metal-catalyzed alkoxycarbonylation according to claim 2, wherein the acid is diluted to 5 mol %.

7. The method for metal-catalyzed alkoxycarbonylation according to claim 1, wherein the solvent is selected from the group consisting of toluene, acetonitrile, and tetrahydrofuran.

8. The method for metal-catalyzed alkoxycarbonylation according to claim 1, wherein the step of heating the reaction mixture comprises heating the reaction mixture to 110-130° C.

9. The method for metal-catalyzed alkoxycarbonylation according to claim 1, wherein the step of placing the reaction mixture under pressure carbon monoxide gas comprises placing the reaction mixture under pressure of at least 20 bar CO.

10. The method for metal-catalyzed alkoxycarbonylation according to claim 9, wherein the pressure is 20-50 bar CO.

11. The method for metal-catalyzed alkoxycarbonylation according to claim 1, wherein the step of heating the reaction mixture is carried out for at least three hours.

12. The method for metal-catalyzed alkoxycarbonylation according to claim 1, wherein the step of heating the reaction mixture is carried out for three to five hours.

13. The method for metal-catalyzed alkoxycarbonylation according to claim 1, wherein the alcohol is selected from the group consisting of methyl alcohol, n-butyl alcohol, 2-ethylhexanol, isobutyl alcohol, isopropyl alcohol, benzyl alcohol, and phenol.

14. The method for metal-catalyzed alkoxycarbonylation according to claim 1, further comprising a step of heating the 2-octendioate diester product in tetrahydrofuran solvent in the presence of a Pd/C catalyst and under flow of hydrogen gas in order to obtain a saturated diester product.

15. The method for metal-catalyzed alkoxycarbonylation according to claim 1, further comprising a step of reacting the 2-octendioate diester product with bis(trifluoromethane)sulfonimide (HNTf$_2$) in the presence of ruthenium acetylacetonate/1,1,1-tris-(diphenylphosphinomethyl)ethane catalyst under pressure of hydrogen gas to obtain a saturated diol product.

16. An alkoxycarbonylated δ-lactone having the formula:

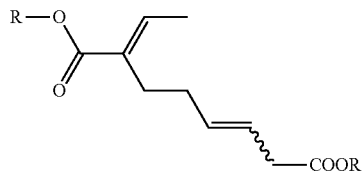

wherein R is selected from the group consisting of methyl, n-butyl, 2-ethylhexanyl, isobutyl, isopropyl, benzyl, and phenyl.

* * * * *